US009068949B2

(12) United States Patent
Cheng et al.

(10) Patent No.: US 9,068,949 B2
(45) Date of Patent: Jun. 30, 2015

(54) SYSTEM AND METHOD FOR MULTIPLEX SPECTROSCOPIC IMAGING

(71) Applicant: Purdue Research Foundation, West Lafayette, IN (US)

(72) Inventors: Ji-Xin Cheng, West Lafayette, IN (US); Mikhail N. Slipchenko, West Lafayette, IN (US); Robert A. Oglesbee, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 14/171,052

(22) Filed: Feb. 3, 2014

(65) Prior Publication Data
US 2014/0218726 A1 Aug. 7, 2014

Related U.S. Application Data

(60) Provisional application No. 61/760,602, filed on Feb. 4, 2013, provisional application No. 61/876,418, filed on Sep. 11, 2013.

(51) Int. Cl.
*G01J 3/28* (2006.01)
*G01N 21/65* (2006.01)
*G01J 3/02* (2006.01)

(52) U.S. Cl.
CPC . *G01N 21/65* (2013.01); *G01J 3/02* (2013.01); *G01J 3/2803* (2013.01)

(58) Field of Classification Search
CPC .............. G01J 3/02; G01J 3/28; G01J 3/10; G01J 3/2823
USPC ................................. 356/300–334
See application file for complete search history.

(56) References Cited

U.S. PATENT DOCUMENTS 5,952,818 A 9/1999 Zhang et al.
6,459,484 B1 * 10/2002 Yokoi ........................... 356/318

(Continued)

OTHER PUBLICATIONS

Bahler et al., "Radical prostatectomy as initial monotherapy for patents with pathologically confirmed high-grade prostate cancer", in the Journal of BJU International, vol. 105, Iss. 10, May 2010, pp. 1372-1376.

(Continued)

*Primary Examiner* — Abdullahi Nur
(74) *Attorney, Agent, or Firm* — Lee & Hayes, PLLC; Christopher J. White

(57) ABSTRACT

A system for measuring an sample includes an illumination source providing electromagnetic radiation pulses at a selected temporal frequency. A microscope focuses the radiation to interact with the sample and produce resultant electromagnetic radiation. A disperser disperses wavelengths of the resultant radiation onto optical sensors, and respective resonant amplifiers amplify signals having the selected temporal frequency. Optical detection apparatus includes the optical sensors, resonant amplifiers, and disperser. The resonant amplifiers amplify portion(s) of their inputs having a selected temporal frequency and attenuate other portion(s). A method of analyzing constituents of a sample includes contemporaneously irradiating the sample with narrowband light and broadband light, the optical power of either modulated at a selected temporal frequency; dispersing wavelengths of resultant light across the optical detectors; and filtering respective signals from the optical detectors to provide spectrum data including signals corresponding to the selected temporal frequency.

18 Claims, 18 Drawing Sheets

(56) References Cited

U.S. PATENT DOCUMENTS

| | | | |
|---|---|---|---|
| 7,623,908 B2 | 11/2009 | Boppart et al. | |
| 7,652,253 B2 | 1/2010 | Zhang et al. | |
| 2002/0152037 A1* | 10/2002 | Sunshine et al. | 702/23 |
| 2008/0094620 A1 | 4/2008 | Li et al. | |
| 2008/0203306 A1 | 8/2008 | Zhang et al. | |
| 2008/0277595 A1* | 11/2008 | Lundquist et al. | 250/458.1 |
| 2010/0213375 A1 | 8/2010 | Loeffler et al. | |

OTHER PUBLICATIONS

Bendell et al., "Single-Cell Mass Cytometry of Differential Immuen and Drug Responses Across a Human Hematopoietic Continuum", in the Journal of Science, vol. 332, May 6, 2011, pp. 687-696.

Bui et al., "Revisiting Optical Clearing with Dimethyl Sulfoxide (DMSO)", In the Journal of Lasers in Surgery and Medicine, vol. 41, 2009, pp. 142-148.

Chan et al., "Reagentless Identification of Single Bacterial Spores in Aqueous Solution by Confocal Laser Tweezers Raman Spectroscopy", in the Journal of Analytical Chemistry, vol. 76, 2004, pp. 599-603.

Cheng et al, "Coherent Anit-Stokes Raman Scattering Microscopy: Instrumentation,Theory, and Applications", in the Journal of Physical Chemistry B, vol. 108, No. 3, 2004, pp. 827-840.

de Juan et al., "Multivariate Curve Resolution (MCR) from 2000: Progres in Concepts and Applications", In the Journal of Analytical Chemistry, vol. 36, Iss. 3-4, 2007, pp. 163-176.

Freudiger, et al., "Label-Free Biodmedical Imaging with High Sensitivity by Stimulated Raman Scattering Microscopy", In the Journal of Science, vol. 322, No. 5909, Dec. 19, 2008, pp. 1857-1861.

Fu et al., "Fast Hyperspectral Imaging with Stimulated Raman Scattering by Chirped Femtosecond Lasers", In the Journal of Physical Chemistry B, Apr. 25, 2013, 14 pages.

Fu et al., "Hyperspectral Imaging with Stimulated Raman Scattering by Chirped Femtosecond Lasers", in the Journal of Physical Chemistry B, vol. 117, 2013, pp. 4634-4640.

Hollricher et al., "High Resolution Optical and Confocal Microscopy", Springer Series in Optical Sciences "Confocal Raman Microscopy", vol. 158, 2011, pp. 1-20.

Hollricher, Olaf, "Raman Instrumentation for Confocal Raman Microscopy", Sprinter Series in Optical Sciences "Confocal Raman Microscopy", vol. 158, 2011, Ch. 3, pp. 43-60.

Jaumot et al., "MCR-BANDS: A user friendly MATLAB program for the evaluation of rotation ambiguities in Multivariate Curve Resolution" In the Journal of Chemometrics and Intelligent Laboratory Systems, vol. 103, Iss. 2, Oct. 15, 2010, pp. 96-107.

Jiang et al., "Penetration kinetics of dimethyl sulphoxide and glycerol in dynamic optical clearing of porcine skin tissue in vitro studied by Fourier transform infrared spectroscopic imaging", In the Journal of Biomedical Optics, vol. 13, 2008, 7 pages.

Lee et al., "Quantitative Image Analysis of Broadband CARS Hyperspectral Images of Polymer Blends", In the Journal of Analytical Chemistry, vol. 83, 2011, pp. 2733-2739.

Lim et al., "Multimodal CARS microscopy determination of the impact of diet on macrophage infiltration and lipid accumulation on plaque formation on ApoE-deficient mice" in the Journal of Lipid Research, vol. 51, Iss. 7, Jul. 2010, pp. 1729-1737.

Lin et al., "Picosecond spectral coherent anti-Stokes Raman scattering imaging with principal component analysis of meibomian glands", in the Journal of Biomedical Optics, vol. 16, Iss. 2, Feb. 9, 2011, 9 pages.

Lu et al., "Multicolor stimulated Raman scattering (SRS) microscopy", In the Journal of Molecular Physics, vol. 110, Aug. 2012, pp. 1927-1932.

Nandakumar et al., "Vibrational imaging based on stiulated Raman scattering microscopy", in the New Journal of Physics, vol. 11, Mar. 25, 2009, 9 pages.

Ozeki et al., "High-speed molecular spectral imaging of tissue with stimulated Raman scattering", In the Journal of Nature Photonics, vol. 6, Dec. 2012, pp. 845-851.

Pegoraro et al., "Hyperspectral multimodal CARS microscopy in the fingerprint region", In the Journal of Biophotonics, vol. 7, 2014, pp. 49-58.

Ploetz et al., "Femtosecond stimulated Raman microscopy", In the Journal of Applied Physics B Lasers and Optics, vol. 87, Iss. 3, May 2007, pp. 389-393.

Potma et al., "Theory of Coherent Raman Scattering", in the Series on Cellular and Clinical Imaging "Coherent Raman Scattering Microscopy", CRC Press, Chs.1.1-1.4, Oct. 29, 2012, 4 pages.

Rinia et al., "Quantitative Label-Free Imaging of Pipid Composition and Packing of Individual Cellular Lipid Droplets Using Multiplex CARS Microscopy", In the Biophysical Journal, vol. 95, Nov. 2008, pp. 4908-4914.

Roberts, et al., "Histology and Pathology of the Human Intervertebral Disc", In the Journal of the Bone and Joint Surgery, Incorporated, vol. 88-A, Suppl. 2, 2006, pp. 10-14.

Saar et al., "Video-Rate Molecular Imaging In Vivo with Stimulated Raman Scattering", In the Journal of Science 3, vol. 330, No. 6009, Dec. 2010, pp. 1368-1370.

Slipchenko et al., "Heterodyne detected nonlinear optical imaging in a lock-in free manner", in the Journal of Biophotonics, vol. 5, Iss. 10 2012, pp. 801-807.

van der Putte, C.J. "Anogenital 'Sweat' Glands: Histology and Pathology of a Gland that Mimic Mammary Glands", in the American Journal of Dermatopahtology, vol. 13, Iss 6, 1997 pp. 557-567.

Wang et al., "Mechanisms of Epi-Detected Stimulated Raman Scatterin Microscopy" in the IEEE Journal of Selected Topics in Quantum Electronics, vol. 18, No. 1, 2012, 5 pages.

Wang et al., "Single cell analysis: the new frontier in 'omics'", Trends in Biotechnology, vol. 28, No. 6, 2010, pp. 281-290.

Wei et al., "Vibrational imaging of newly synthesized proteins in live cells by stimulated Raman scattering microscopy", In the Journal of PNAS, vol. 110, No. 28, Jul. 9, 2013, pp. 11226-11231.

Woodbury, et al., "Ruby Laser Operation in the Near IR", In the Proceedings of the IRE, Nov. 1962, 19 pages.

Zhang et al., "Highly Sensitive Vibrational imaging by Femtosecond Pulse Stimulated Raman Loss", In the Journal of Physical Chemistry Letters, vol. 2, 2011, pp. 1248-1253.

Zhang et al., "Quantitative Vibrational Imaging by Hyperspectral Stimulated Raman Scattering Microscopy and Multivariate Curve Resolution Analysis", In the Journal of Analytical Chemistry, vol. 85, Iss. 1, Jan. 2, 2013, pp. 98-106.

\* cited by examiner

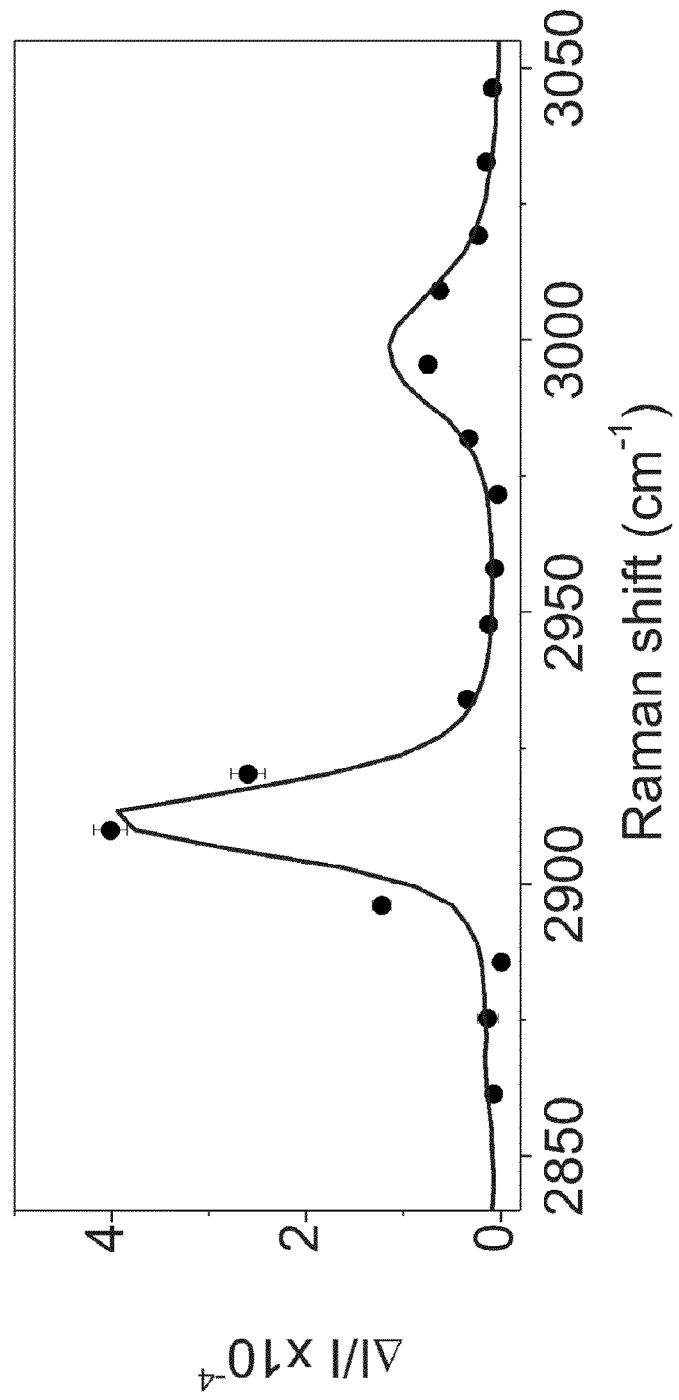
FIG. 9A
FIG. 9B

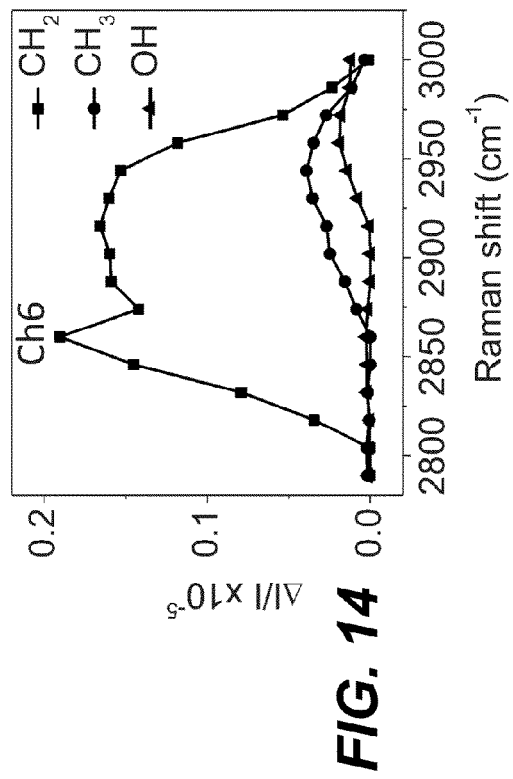
FIG. 13
FIG. 14
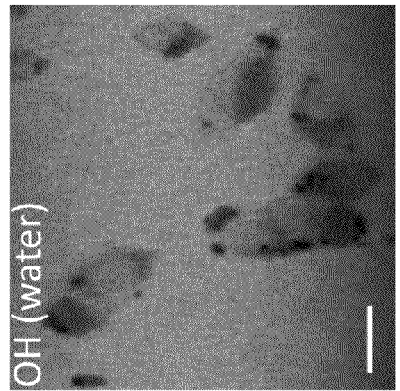
FIG. 15C
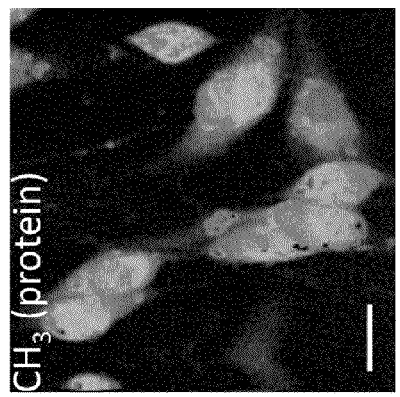
FIG. 15B
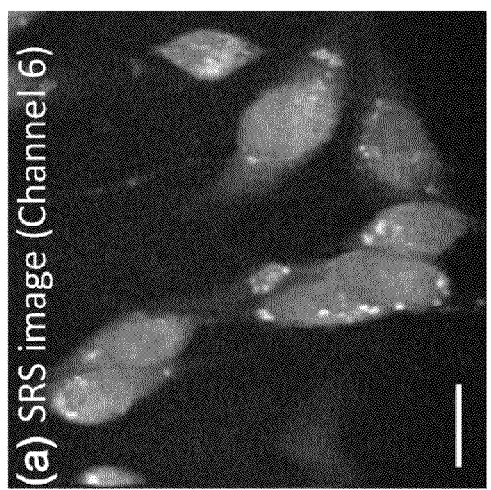
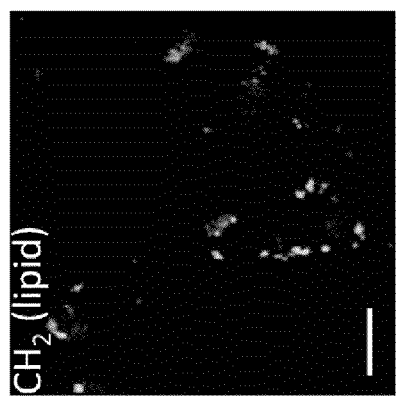
FIG. 15A

SYSTEM AND METHOD FOR MULTIPLEX SPECTROSCOPIC IMAGING

CROSS-REFERENCE TO RELATED APPLICATIONS

This nonprovisional application claims the benefit of U.S. Provisional Patent Application Ser. No. 61/760,602, filed Feb. 4, 2013 and entitled "Cell Machinery via Spectroscopic Imaging," and of U.S. Provisional Patent Application Ser. No. 61/876,418, filed Sep. 11, 2013 and entitled "Spectroscopic Detector and System," the entirety of each of which is incorporated herein by reference.

STATEMENT OF FEDERALLY SPONSORED RESEARCH OR DEVELOPMENT

This invention was made with Government support under Contract No. GM104681 awarded by the National Institutes of Health. The government has certain rights in the invention.

TECHNICAL FIELD

The present application relates to spectroscopy, and more particularly to improved spectroscopic detectors.

BACKGROUND

Chemically selective imaging platforms are important for monitoring biological processes such as drug penetration into tissues and metabolite conversion in live cells. Light can be used in such platforms since electromagnetic radiation is modified in various ways when it passes through a substance or reflects off the substance. Various compounds and other chemical structures, such as atomic bonds, can be detected by locating absorption bands in the light from the substance. Raman scattering is an effect in which light of an incident wavelength strikes an object and the object radiates light of a slightly different wavelength. The difference between the wavelengths is correlated with the energy of an electron band in the object.

Bio-analytical measurement techniques, including Raman spectroscopy, NMR spectroscopy and mass spectroscopy, are widely used for the molecular detection, further leading to deeper research in histology and cell mechanisms. These and other schemes analyze the spectra of complex objects. For example, confocal-fluorescence spectral imaging provides two-dimensional images of an object, e.g., a cell, at each of a number of wavelengths. However, these sets of images can be time-consuming to acquire, e.g., five seconds per wavelength for some techniques. This limits the usefulness of these techniques for live cells, which can move during imaging.

Moreover, many prior schemes are limited to the single point detection without spatial distribution of molecules. There is thus a need for high resolution imaging tools combined with molecular mapping ability. Raman-scattering-based spectroscopic imaging has found wide use in biomedical, pharmaceutical, and material sciences due to its high chemical selectivity and noninvasive nature. However, because spontaneous Raman scattering is a feeble effect, the imaging speed of Raman microscope is limited to hundreds of milliseconds per pixel, or tens of seconds per frame. Such slow data acquisition speed inhibits the application of Raman microscopy to live imaging or large-area mapping. For example, confocal Raman microscopes that provide sub-micron resolution and selective-chemical mapping have been used, but such microscopes have a low scattering cross section, especially to dynamic systems.

Multiplex coherent anti-Stokes Raman scattering (CARS) microscopy is a scheme that provides a spectrum at each pixel. The CARS signal is generated at a frequency different from the frequency of the incident light, so multiplex CARS detection is straightforward using a sensitive charge coupled device. Multiplex CARS microscopy based on broadband excitation and parallel spectral detection has been demonstrated with the pixel dwell time as short as 20 ms. However, this speed does not permit imaging of a highly dynamic living system. Moreover, the CARS signal contains a non-resonant background that makes quantitative analysis difficult. Hyperspectral CARS or SRS microscopy has been demonstrated by spectral scanning of a narrowband laser and collection of images at a series of Raman shifts. Nevertheless, this approach is not applicable to living systems due to spectral distortion caused by dynamics inside live cells during the period of spectral scanning. Moreover, CARS can have difficulty detecting chemical bonds such as a C—H bond.

The Stimulated Raman Scattering (SRS) process has recently been employed for high-speed vibrational imaging. SRS provides strong Raman signal and exhibit no non-resonant background. SRS is a third order nonlinear optical process, which involves two laser fields, namely a pump field at $\omega_p$ and a Stokes field at $\omega_S$. When the beating frequency ($\omega_p - \omega_S$) is tuned to excite a molecular vibration, the energy difference between $\omega_p$ and $\omega_S$ pumps the molecule from a ground state to a vibrationally excited state. The laser field manifests this as a weak decrease of pump beam intensity, called stimulated Raman loss (SRL), and corresponding increase of Stokes beam intensity, called stimulated Raman gain (SRG). Using heterodyne detection, SRS is able to offer quantitative spectral information with a pixel dwell time of few μs.

FIG. 6 shows an example of SRS measurement of a sample according to conventional schemes. The angular frequency $\omega_p$ of a narrowband pump beam is scanned and the angular frequency $\omega_s$ of a narrowband Stokes beam is held fixed. With $\omega_p - \omega_S$ tuned to a molecular vibration at frequency $\Omega_n$, n∈[1, 2, 3], the pump beam intensity is slightly decreased by stimulated Raman loss (SRL; $\Delta I_P$) and the Stokes beam intensity is slightly increased by stimulated Raman gain (SRG; $\Delta I_S$). Only parts of the spectrum at which SRL occurs are illustrated here. Dashed lines show the incident radiation before interaction with the sample; solid lines show the radiation resulting from interaction with the sample.

To measure the weak laser intensity change $\Delta I_p$, e.g., on the order of 0.01% or smaller, a heterodyne detection approach has been used. In the case of SRL, the Stokes beam intensity $I_S$ is modulated and the pump beam intensity $I_p$ is recorded by a photodiode. The induced modulation is then extracted by a lock-in amplifier. Theoretically, the modulation depth induced by SRL, $I_{SRL}/I_p$, is linearly proportional to the Raman cross section, σ, molar concentration of the target molecule, N, and the Stokes beam intensity, i.e., $$I_{SRL}/I_p \propto \sigma N I_S. \tag{1}$$

A megahertz (MHz) modulation rate can be used to reduce effects of low frequency laser noise. Lock-in amplifiers (analog or digital) are commonly used for extraction of heterodyne-detected signals like SRS. So far, fast SRS imaging is mostly implemented by narrowband laser excitation of single isolated Raman band. Single-color SRS is, however, not able to resolve overlapping Raman bands contributed by target molecules and background tissue components. Moreover, the imaging of living systems using SRS is made more difficult by the movement of objects during the wavelength tuning. Multi-color SRS imaging has been demonstrated by using three lock-in amplifiers. Such a scheme is, however, impractical for acquisition of a complete Raman spectrum due to high cost of radio-frequency (RF) lock-in amplifiers.

There is, therefore, a need of improved ways of collecting spectral data of samples such as objects, tissue, or microorganisms, and particularly of collecting spectral data over areas of such samples.

Reference is made to WO2013/110023, International Application No. PCT/US2013/022348, U.S. Pat. No. 6,809,814, and U.S. Pat. No. 6,108,081, each of which is incorporated herein by reference.

BRIEF DESCRIPTION

According to an aspect, there is provided a system for measuring an sample, the system comprising:
a) an illumination source adapted to provide electromagnetic radiation pulses, the providing having a selected temporal frequency;
b) a microscope adapted to focus the provided electromagnetic radiation onto the sample, so that resultant electromagnetic radiation is produced by an interaction of the provided electromagnetic radiation with the sample;
c) a plurality of optical sensors;
d) a disperser adapted to disperse wavelengths of the resultant electromagnetic radiation onto the plurality of optical sensors; and
e) a plurality of resonant amplifiers corresponding to respective ones of the optical detectors, each resonant amplifier operative to amplify signals having the selected temporal frequency.

According to another aspect, there is provided optical detection apparatus, comprising:
a) a plurality of optical sensors configured to provide respective electrical signals corresponding to respective incident electromagnetic radiation;
b) a plurality of resonant amplifiers corresponding to respective optical detectors, each resonant amplifier operative to amplify portion(s) of the respective electrical signal having a selected temporal frequency and to attenuate portion(s) of the respective electrical signal not having the selected temporal frequency; and
c) a disperser adapted to receive light and distribute a respective selected portion of an optical bandwidth of the received light to each of the plurality of optical sensors.

According to still another aspect, there is provided a method of analyzing constituents of a sample, the method comprising:
contemporaneously irradiating the sample with incident radiation including narrowband light and broadband light;
while irradiating the sample, modulating the optical power of the narrowband light or the broadband light at a selected temporal frequency;
dispersing wavelengths of resultant light from the sample across a plurality of optical detectors; and
filtering respective signals from the optical detectors to provide a spectrum dataset of the sample, the spectrum dataset including signals corresponding to the selected temporal frequency.

Various embodiments advantageously provide a spectroscopic imaging device using parallel lock-in free detection of spectrally dispersed stimulated Raman scattering (SRS) signal. Using a tuned amplifier array, various aspects herein permit spectral data acquisition at the speed of 30 microseconds per pixel, which is faster than multiplex CARS by three orders of magnitude. Various aspects use multivariate curve resolution (MCR) analysis, e.g., to monitor molecular penetration into skin tissue in real time and perform spectroscopic imaging of single living cells.

This brief description is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein:

FIGS. 9A and 9B show experimental data of determining Raman shifts using the system calibrated as described above with reference to FIGS. 8A and 8B, FIG. 9A including a graphical representation of micrographs;

FIGS. 13, 14, and 15A-15C show experimental data of multiplex SRS imaging of living Chinese hamster ovary (CHO) cells, FIGS. 13 and 15A-15C including graphical representations of micrographs;

Figure 1:
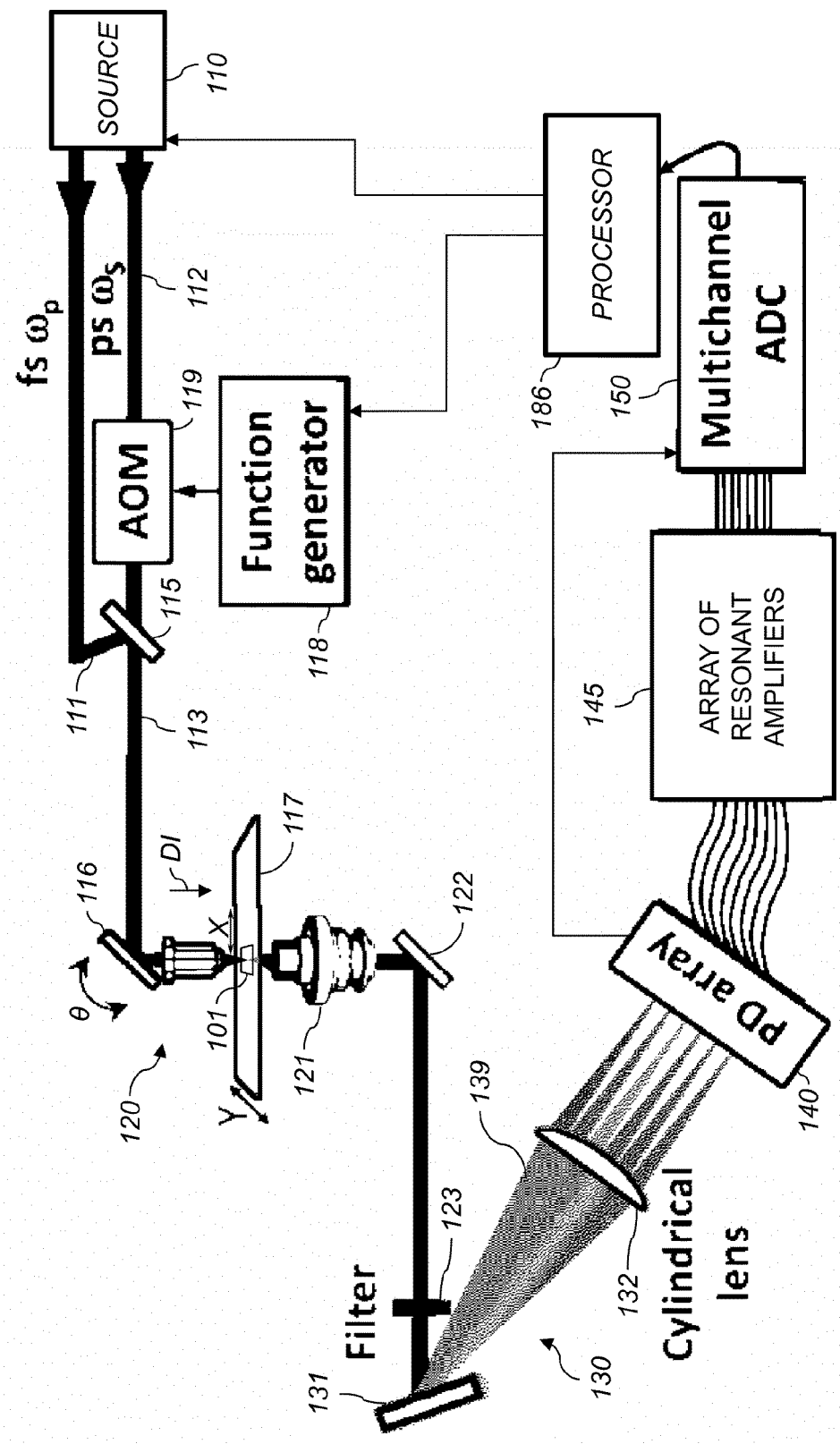
FIGS. 1-3 show exemplary systems for measuring samples.

The attached drawings are for purposes of illustration and are not necessarily to scale.

DETAILED DESCRIPTION

As used herein, the terms "optical" and "light" and the like refer to electromagnetic radiation generally, and are not limited to the visible wavelength range (~400 nm-700 nm) or another wavelength or frequency range, unless explicitly noted.

In the following description, some aspects will be described in terms that would ordinarily be implemented as software programs. Those skilled in the art will readily recognize that the equivalent of such software can also be constructed in hardware, firmware, or micro-code. Because data-manipulation algorithms and systems are well known, the present description will be directed in particular to algorithms and systems forming part of, or cooperating more directly with, systems and methods described herein. Other aspects of such algorithms and systems, and hardware or software for producing and otherwise processing the signals involved therewith, not specifically shown or described herein, are selected from such systems, algorithms, components, and elements known in the art. Given the systems and methods as described herein, software not specifically shown, suggested, or described herein that is useful for implementation of any aspect is conventional and within the ordinary skill in such arts.

Fast spectroscopic imaging advantageously permits in situ analysis of target molecules in a highly dynamic environment. Various aspects permit direct visualization of chemistry that occurs at microsecond time scale.

Various aspects advantageously provide improved filter performance compared to lock-in amplifiers when the pixel dwell time is down to the order of a few μs, which corresponds to a few hundred kHz measurement rate. Various aspects provide SRS signals at MHz laser modulation frequency, then extract and amplify those signals, using a resonant circuit, and then rectify the extracted, amplified signals for digitization. Because the resonant circuit can be a chip as small as a penny, an array can be made to allow for parallel acquisition of multiple signals. Herein is described a tested 16-channel tuned amplifier (TAMP) array permitting parallel detection of spectrally dispersed SRS signals with 30 μs pixel dwell time. This permits spectroscopic imaging of highly dynamic living systems as well as separation of SRS signal from unwanted background based on multivariate analysis of spectra acquired at each pixel. Various aspects increase imaging speed by more than three orders of magnitude compared to spontaneous Raman microscopes, while providing label-free, background-free spectrum data corresponding to spontaneous-Raman data.

A 16-channel parallel-detection SRS system was constructed and spectroscopic imaging of live cancer cells was performed. The system included a main circuit board to which the HAMAMATSU photodiode array was connected. Sixteen TAMPs were constructed on individual circuit boards that plugged in to the main circuit board. Parallel detection of dispersed SRS signals with 30 μs pixel dwell time was performed; this dwell time is ~1000 times faster than the current multiplex CARS microscope. Three basic chemical components, namely protein, water and lipid, were successfully extracted at pixel dwell time of 30 μs, which is 5000 times faster compared with the fastest Raman microscope. A 32-channel multiplex SRS microscope with a pixel dwell time of 20 μs described. Compared to the lock-in-amplifier-based detectors, various aspects reduce the cost of detection electronics by two orders of magnitude while being easily integrated. Parallel detection can be readily integrated and installed in a microscope, e.g., from OLYMPUS or LEICA, of the type typically used for CARS microscopy. Using narrowband resonant amplifiers, various aspects permit extraction of a single frequency SRS signal with high sensitivity and high speed. Various aspects described herein permit measuring Raman or other spectra over a large area in a short amount of time, e.g., two seconds for multiple wavelengths.

Various aspects provide improved data collection for histology and pharmaceutics. Due to the strong correlation between histological changes and clinical diseases, histology has become one of the most powerful tools in pathology. In hospitals and reference laboratories, histology-based diagnostics are widely used. In practice, the de-hydration process of the standard histology using hematoxylin and eosin stains could remove parts of potential molecular markers. For instance, lipophilic molecules, which are a potential marker for cancer aggressiveness, are washed away during de-hydration. In addition, traditional histology and biopsy are based on morphologic observation. Imaging systems described herein provide quantitative analysis in histology through molecular mapping with sub-micron resolution. This assists pathologists in assessing abnormal or aggressive tissue from biopsy in a label-free manner with high accuracy.

Regarding pharmaceutics, formulation study, as the foundation of drug development, involves characterization of each component including chemical and physical properties in a solid dosage forms. These factors play a key role in the determination of bioavailability as well as activity of a drug. Various aspects herein permit determining physical properties such as particle size by extracting data from morphologic images, and chemical properties such as degradation of each component can be determined using the quantitative chemical-bond mapping data. SRS parallel-detection technology described herein can be integrated into a commercialized microscope.

Throughout this document, references to times (s) or frequencies (Hz) refer to the time domain, i.e., how photons are emitted over time. Operations described as being performed in the time domain can also be performed in the temporal-frequency domain, e.g., using appropriate Fourier transforms to move between time and temporal-frequency domains. References to wavelength (nm) or wavenumber ($cm^{-1}$) refer to the spectral (energy) domain, i.e., the energies of the emitted photons. References to bandwidth (Hz, nm, or $cm^{-1}$) refer to the domain indicated by the contexts of the references.

FIG. 1 shows an exemplary system for measuring a sample 101. In FIG. 1 and subsequent figures, dithered hatching is used to indicate that multiple wavelengths of electromagnetic radiation are present or are being considered, or to show the paths of radiation beams hidden behind structures in the views as shown. Various methods of detection can be performed using the structures described in this and subsequent figures.

Illumination source 110 is adapted to provide electromagnetic radiation pulses, e.g., broadband or narrowband optical radiation pulses. The providing has a selected temporal frequency. That is, source 110 provides pulses of a selected type or wavelength of radiation at regular time intervals defined by the selected temporal frequency. In the example shown, source 110 includes a two-output laser. For example, an INSIGHT DEEPSEE from NEWPORT SPECTRA-PHYSICS can provide laser pulses <120 fs long that have spectral content over the wavelength range from ~700 nm to ~1300 nm. The terms "broadband" and "narrowband," as used herein to describe beams such as beams 111, 112, are relative and do not require that those beams have any particular spectral breadth or spectral-domain full width at half maximum (FWHM). Broadband radiation has a broader spectrum at photon counts above the noise level than does than narrowband radiation.

A system was constructed according to an exemplary aspect. A tunable 80 MHz pulsed laser (INSIGHT, SPECTRA PHYSICS) source 110 provided two synchronized outputs. The tunable beam with up to 1.0 W power, 120 fs pulse duration, and tuning range from 680 to 1300 nm served as the pump beam 111. The fixed 1040 nm beam with 0.5 W power and ~200 fs pulse width served as the Stokes beam 112. The Stokes beam 112 was temporally modulated at 2.6 MHz by an acoustic-optical modulator (AOM) 119 and sent into a pulse shaper 210 (FIG. 2) to narrow down the spectral-domain bandwidth to 5-20 $cm^{-1}$. As a result, beam 111 was a broadband pump beam and beam 112 was a narrowband Stokes beam. The synchronized pump and Stokes beam were aligned by semi-silvered mirror 115 to provide beam 113 of the narrowband and broadband electromagnetic radiation. Beam 113 can be directed via mirror 116, which can be rotatable by angle θ, into microscope 120, e.g., a laser-scanning microscope. AOM 119 can be controlled by function generator 118, which can itself be controlled by processor 186. Other broad-wavelength sources than a laser can also be used.

According to this and other exemplary aspects, illumination source 110 includes a narrowband source, a broadband source, and a combiner (e.g., mirror 115) for providing the electromagnetic radiation pulses including electromagnetic radiation from both the narrowband source and the broadband source.

In various aspects, processor 186 is configured to temporally modulate an output power of the narrowband source or an output power of the broadband source (or both) at the selected temporal frequency. In an example, the Stokes beam 112 is modulated. The pump beam 111 can be modulated or not, and can be provided or not while the Stokes beam 112 is not being provided. For example, the narrowband source can be configured to provide infrared light (e.g., 1040 nm) as the electromagnetic radiation from the narrowband source, and the broadband source can be configured to provide light including visible and infrared wavelengths (e.g., 680-1300 nm) as the electromagnetic radiation from the broadband source.

Microscope 120 is adapted to focus the provided electromagnetic radiation onto the sample 101. Resultant electromagnetic radiation is thus produced by an interaction of the provided electromagnetic radiation with the sample 101. For example, the provided electromagnetic radiation can be transmitted through or reflected, refracted, or diffracted by the sample. Microscope 120 can have any optical configuration. In an example, the light is collected by oil condenser lens 121 in the forward direction. The light can be reflected by mirror 122 and filtered by filter 123. In this example, resultant radiation beam 139 is shown.

Optical sensors 140 in a plurality of optical sensors (e.g., >1 sensor or >2 sensors) are configured to detect electromagnetic radiation. Disperser 130 is adapted to disperse wavelengths of the resultant electromagnetic radiation onto the optical sensors 140. There can be some wavelengths or optical sensors that are not used; e.g., the plurality of optical sensors 140 can only include the odd channels of a photo-diode array. In various aspects, disperser 130 is adapted to distribute a respective selected portion of the spectral (e.g., optical) bandwidth of the received electromagnetic radiation to each of the plurality of optical sensors 140. Disperser 130 can include diffraction grating 131. An exemplary disperser 130 was constructed using a 1200 groove/mm grating 131 and a 1 meter focal length lens 132. Optical sensors 140 were elements of a photo-diode array. The dispersed pump beam had 180 $cm^{-1}$ bandwidth in the spectral domain and covered the photo-diode array (see FIG. 8B, discussed below, and note that 790 nm-800 nm is a range of ~158 $cm^{-1}$). The tested photo-diode array was an S4114-35Q by HAMAMATSU. Each photodiode is 0.9 mm wide by 4.4 mm high; the disperser disperses light across the width of the array. The tested array had 35 channels, of which the first 16 odd-numbered channels were used.

Figure 4:
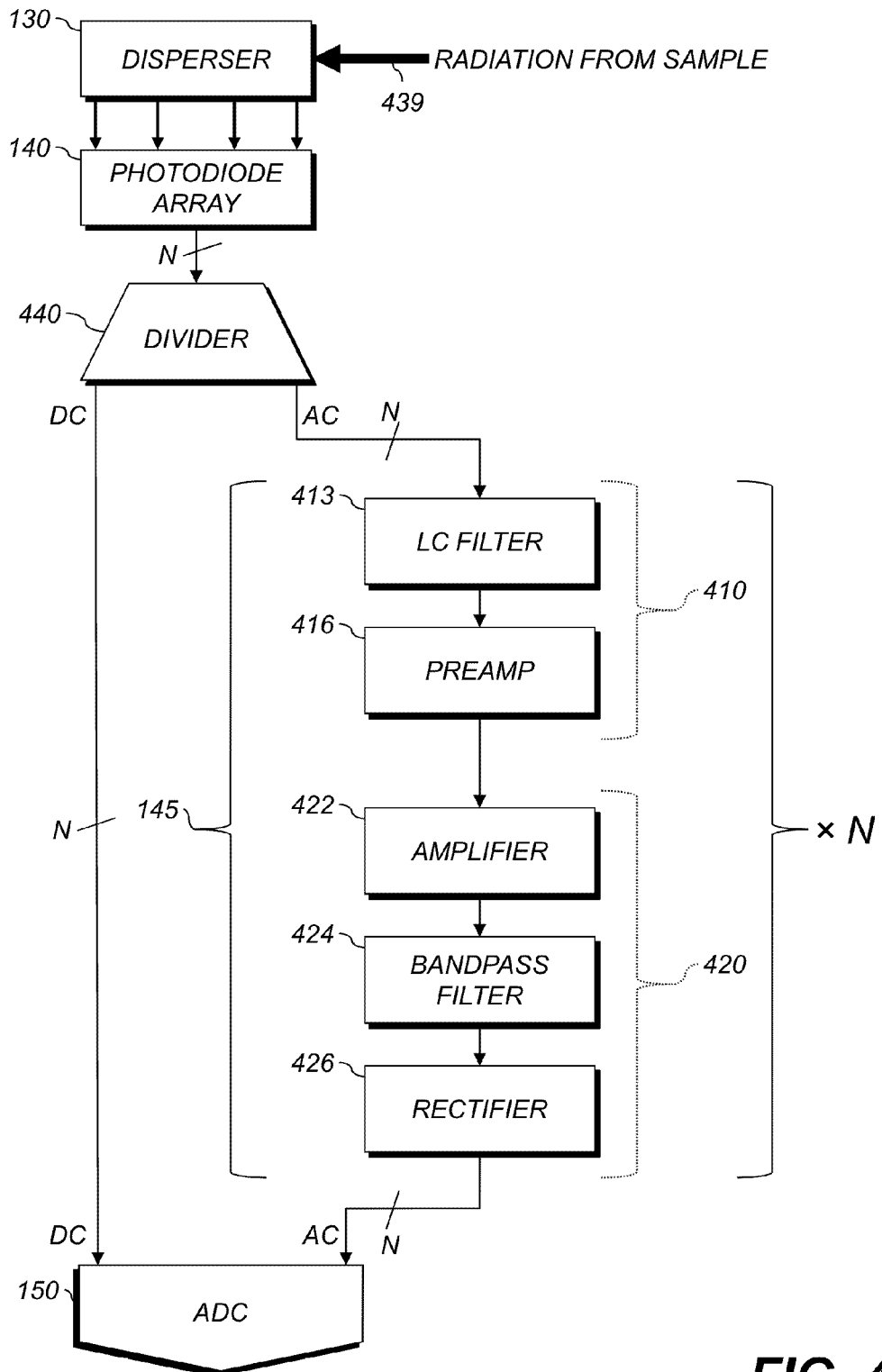
FIG. 4 shows a block diagram of optical detection apparatus according to various aspects.

A plurality of resonant amplifiers 145 correspond to respective ones of the optical detectors 140. The photocurrent or other output from each optical detector (e.g., photo-diode) 140 is provided to one or more resonant amplifiers 145. Each resonant amplifier is operative to amplify signals having the selected temporal frequency at which at least some of the electromagnetic radiation is provided by source 110. FIG. 4, discussed below, provides more details of a configuration of resonant amplifier 145 referred to as a tuned amplifier (TAMP). Signals from resonant amplifiers 145 are detected, e.g., by a multichannel analog-to-digital converter (ADC) 150 or multichannel ADC board, which provides digital data corresponding to the signals to processor 186. In a tested example, the amplified AC signals from resonant amplifiers 145 were collected by an 80-channel NATIONAL INSTRUMENTS PCI-6255 capable of up to a 1.25 MS/s acquisition rate. As indicated, signals from the optical sensors 140 can also be provided directly to ADC 150, e.g., to measure DC (temporal) components of optical signals. Processor 186 can control the operation of source 110, function generator 118, and AOM 119.

Various aspects detect multiple wavelengths of light at once. This advantageously permits discriminating between signals arising from overlapping responses of the analyte. For example, the analyte can include multiple substances that exhibit some overlapping Raman shifts. Measuring at multiple wavelengths can permit discriminating such substances. The high speed of various aspects described herein advantageously permits measuring living systems such as cells, tissues, prostate cancer cells, or plants. Measurements can be taken while a drug or other active agent is administered to determine the response of the living system to the drug. Fixed samples and specimens, e.g., minerals, can also be measured.

In various aspects, a hybrid-scanning technique is used. "Scanning" of a laser or sample in a direction refers to moving the laser or sample, e.g., back and forth, in that direction. The laser can be rasterized over the sample by moving the sample perpendicular to a direction in which the laser is scanned. In an example, in a dimension perpendicular to a dispersion plane of disperser 130, 1-D laser scanning can be used. A single-mirror scanning laser can be scanned in the X direction by motion of rotatable mirror 116. The X direction can be perpendicular to the dispersion plane of grating 131; e.g., disperser 130 can include grating 131 arranged to disperse light perpendicular to the X direction. The second (Y) dimension can be scanned by a motorized stage 117 which can move the sample 101, e.g., with a velocity of 1 mm/second, thus permitting imaging with a few μs pixel dwell time. In this and other aspects, the system can include a scanner (in this example, mirror 116 and stage 117) for scanning a focal point of the provided electromagnetic radiation (beam 113) across the sample 101 in an X direction and scanning the sample 101 in a Y direction. Hybrid scanning, including laser scan in one dimension and sample scan in another dimension, advantageously reduces perturbation of spectral dispersion on the grating. Moreover, hybrid scanning permits scanning the laser very rapidly, reducing the laser energy per pixel. This can advantageously permit more delicate tissues to be imaged without damage.

In various aspects, the microscope 120 is arranged so that the sample 101 is illuminated by the provided electromagnetic radiation from a first direction DI and the disperser 130 is arranged downstream of the sample along the first direction DI. This is a forward-detection configuration in which light transmitted through sample 101 is measured. The microscope can include one or more focusing lenses, and can include a confocal optical system such as that used in a confocal microscope.

Various aspects include detection systems that can be attached to existing confocal or other microscopes. Various aspects include purpose-built microscopes. Light sources and detection units can be provided together or separately. Since the TAMPs do not require lock-in with the light source, various light sources can be used.

Various components can be used in systems described herein. Examples include: electronics components (inductors, capacitors, op amps, etc); data acquisition cards with, e.g., PCI interfaces; and optical components (mirrors, mounts, gratings, lenses, objectives, etc). The electronics components can be used to build a 32-channel TAMP array and a photo-diode array. The data acquisition cards can be used to collect AC and DC signals from a (e.g., 32-channel) TAMP array. This is discussed below with reference to FIG. 4. Multiplex SRS microscopes according to various aspects described herein can use various tunable laser sources, motorized stages, upright microscopes or computers.

Figure 2:
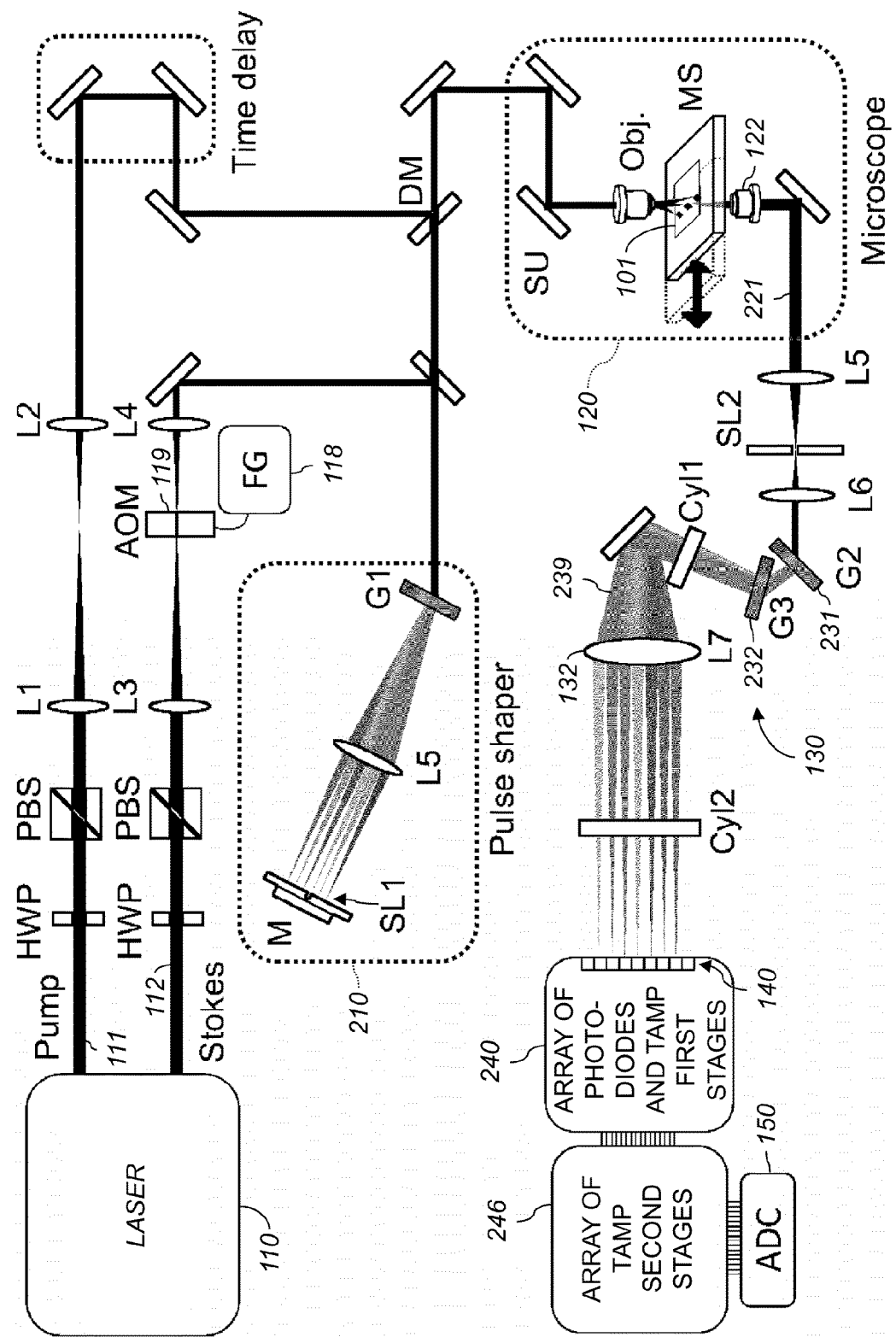

FIG. 2 shows another exemplary system for measuring a sample 101. The system can be a spectroscopic SRS microscope using broadband laser excitation and parallel detection. The following abbreviations are used: HW: half wave-plate, PBS: polarizing beam splitter, AOM: acoustic optical modulator, FG: function generator, L: lens, DM: dichroic mirror, G: grating, SL: slit, M: mirror, SU: scanning unit, OBJ: objective, MS: motorized stage, C: condenser, CL: cylindrical lens.

A multiplex SRS microscope according to an exemplary aspect was constructed. The broadband local oscillator (resultant radiation beam 221) which carried SRL spectral information was dispersed on a 35-channel photodiode array 240. In a tested configuration, 16 resonant amplifiers 145 in the TAMP configuration were used to extract the narrowband SRL signal for each odd-numbered channel (1, 3, 5 . . . ) of photodiode array 240. Other configurations of resonant amplifier can be used.

The multiplex SRS microscope used hybrid scanning of specimens and parallel detection of spectrally dispersed SRS signals. Source 110 is as described above. The Stokes beam 112 was modulated at 2.1 MHz by an acoustic-optical modulator (AOM) 119 (in a tested configuration, driven by function generator 118) and sent into a pulse shaper 210 to narrow down the spectral (energy-domain) width. Slit SL1 in pulse shaper 210 only permits that narrow portion of the light to pass. The full width at half maximum was measured to be 2.3 ps by an autocorrelator and the power was 50 mW after the pulse shaper. The pump and Stokes beams 111, 112 were collinearly combined and directed into a laser-scanning microscope 120. For SRL imaging, the pump beam was collected by an oil condenser 121 in forward direction, and dispersed by two diffraction gratings 231, 232 (in a tested configuration, each 1200 groove/mm). Using a 1.0 meter focal length lens 132, the dispersed pump beam 239 with 180 $cm^{-1}$ spectral bandwidth was covered by a photodiode array (S4114-35Q, HAMAMATSU, each element is 0.9 mm×4 mm). Two cylindrical lenses, combined with the 1.0 meter focal length lens 132, were used to conjugate the plane on the photodiode array 140 to the back aperture of the condenser 121.

In a tested configuration, the photocurrent from each photodiode was sent into first stage 410 (FIG. 4) of the TAMPs integrated with the photodiodes 140 in array 240, and then into second stage 420 (FIG. 4) in array 246. The resulting amplified AC signals were collected by a 80-channel ADC 150 board (NI, PCI-6255) with 1.25 MS/s (million samples per second) acquisition rate. In the example shown, the TAMPs were divided into a first stage 410 (FIG. 4) positioned electrically nearer the photodiodes 140, and shown as included in array 240, and a second stage 420 (FIG. 4) positioned electrically farther from the photodiodes 140 and shown as array 246. A hybrid-scanning scheme was used to maintain the spectral information. 1-D laser scanning was implemented in the dimension perpendicular to the dispersion plane. The second dimension was scanned by a motorized stage which could move at a velocity of 1.0 mm/second. This hybrid scanning scheme permitted fast imaging with pixel dwell time down to 30 μs.

Disperser 130 included the G2-G3-Cyl1-L7-Cyl2 path to separate different wavelengths of light. Each photodiode in a linear photodiode array 240 thus receives a different range of wavelengths of light, e.g., 11-13 $cm^{-1}$ wide. In an example, the light source has an optical bandwidth of 200 $cm^{-1}$, and each of 16 sensors receives approximately 12.5 $cm^{-1}$ of that bandwidth. A 128-channel photodiode array 240 can also be used, e.g., at ~6 $cm^{-1}$ per photodiode, covering an optical bandwidth of ~768 $cm^{-1}$ or ~800 $cm^{-1}$. The optical source can be selected or designed to provide light of a given optical (spectral) bandwidth. The disperser can be designed to direct a selected portion of that spectral bandwidth to each of a selected number of sensors. The disperser can be designed according to the analyte to be detected, e.g., to have higher or lower resolution. Photodiode arrays (e.g., from HAMAMATSU) can be used, as can individual photodiodes, CCD sensors, or other sensors.

Figure 3:
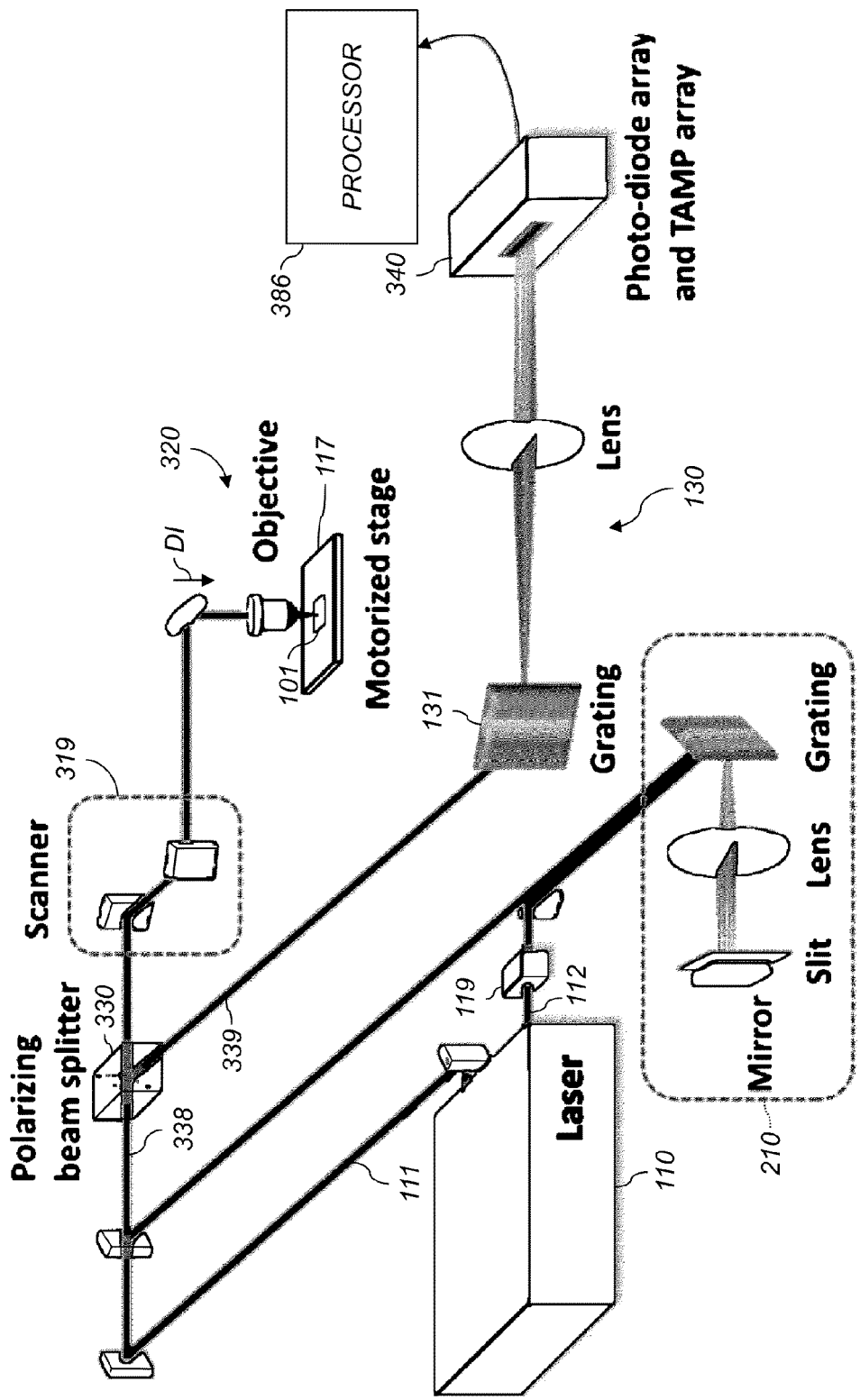

FIG. 3 shows another exemplary system for measuring a sample 101. The illustrated system is an epi-detected multiplex SRS imaging system in which light reflected from sample 101 is measured. Source 110 is as discussed above with reference to FIG. 2. Stokes beam 112 is modulated at, e.g., 2.1 MHz by AOM 119. Pulse shaper 210 narrows down the spectral bandwidth to, e.g., 5~20 $cm^{-1}$. The synchronized pump and Stokes beams 111, 112 are provided to microscope 320. In this and other epi-detection aspects, microscope 320 is arranged so that the sample 101 is illuminated by the provided electromagnetic radiation from a first direction DI, the disperser is arranged upstream of the sample 101 along the first direction DI, and the system further includes a beam splitter (e.g., polarizing beam splitter 330) arranged between the sample 101 and the disperser 130.

Using backward (epi) detected SRL for tissue imaging permits imaging without being limited by the speed of a stage. This permits frame rates fast enough for large area mapping, e.g., in histology studies. Epi-detection also permits imaging of thick-sliced tissues, tablets, or other non-transparent samples, as well as in-vivo samples. In an epi-detection scheme, the signal propagates back through the optical path and can be separated from the excitation beams after it passes back through scanning mirrors (so called de-scanned detection). Since the local oscillator is de-scanned, a two-dimensional laser scan can be adopted, e.g., using two-dimensional scanning mirrors. The frame rate of an image with 500×500 pixels, covering 300 µm×300 µm, can be increased to less than 1 s. The motorized stage in that case can be used to move the sample in 300 µm steps in X or Y. For example, for large area mapping, where the area is larger than field of view of the objective used, the stage can move the sample to various positions. After collecting images at different nearby positions the large image can be composed. For example, to obtain a 1.5 mm×1.5 mm image, 25 images of 300 µm×300 µm can be captured. Large area mapping can be conducted in, e.g., less than 1.0 min for a 1.5 mm×1.5 mm area. By analyzing potential markers, for example, cholesterol stored in a lipid droplet, diseased tissue can be identified via quantitative analysis of potential markers based on spectroscopic information.

In an exemplary configuration, a 25× water immersion objective with a large numerical aperture (N.A.=1.05, Olympus) can be used to provide a large field of view (300 µm×300 µm) and efficient collection of back-scattered photons. Polarizing beam splitter 330 can be used to separate the back-scattered de-scanned local oscillator (resultant radiation beam 339) from the original combined pump-and-Stokes beam 338. The resultant radiation beam 339 can be dispersed by diffraction grating 131 in disperser 130 and collected by 32-channel photo-diode array 140 in detector 340. The SRS signal can be extracted by a 32-channel TAMP array in detector 340 and sent to ADC boards (not shown), and thence to processor 386.

Scanner 319, e.g., having a pair of galvanometer mirrors, scans the laser in two dimensions (e.g., X and Y). Scanner 319, together with sample scanning using a motorized stage 117, permits large-area mapping to be performed, e.g., covering 1.5 mm×1.5 mm in less than one minute. This and other aspects herein permit quantification of metabolites and other bio-molecules in an intact tissue, e.g., spectroscopic imaging for histology studies. For example, nonlinear imaging of human prostate cancer tissue can be performed using microscopes described herein. Epi-detected multiplex SRS can be applied to histology study such as large-area mapping result of prostate cancer tissues.

FIG. 4 shows a block diagram of optical detection apparatus including resonant amplifiers 145 and related components according to various aspects. Disperser 130 disperses resultant radiation beam 439 (e.g., a light beam) across a plurality of optical sensors, as discussed above. Each sensor can include a photodiode. In various aspects, disperser 130 is adapted to receive light and distribute a respective selected portion of an optical bandwidth of the received light to each of the plurality of optical sensors. In this example, the optical sensors are elements of photodiode array 140. In various aspects, the optical sensors are configured to provide respective electrical signals corresponding to respective incident electromagnetic radiation.

In various aspects, the electrical signals are provided directly to tuned amplifiers 145. In other aspects, the electrical signals are filtered or otherwise processed by a divider 440. In the example shown, divider 440 passes AC components of signals from each photo-diode, i.e., components having temporal frequencies that are greater than 0 Hz and that substantially correspond to the modulation of Stokes beam 112 (e.g., ~2.1 MHz), to the resonant amplifiers 145. Divider 440 passes DC components of signals from each photo-diode, i.e., signals proportional to the average laser beam power at the photodiode (temporal frequency close to 0 Hz, e.g., 0 Hz-10 kHz). directly to ADC 150. The DC components correspond to the intensity of the local oscillator is directly sent to the analog-to-digital converter (ADC) board. Divider 440 can be a passthrough or fan-out element or can include low-pass/high-pass filters. ADC 150 can also or alternatively include such filters.

Accordingly, in various aspects, ADC 150 is an analog-to-digital conversion unit adapted to provide digital data of respective high-frequency signals from the resonant amplifiers and of respective low-frequency signals from the optical sensors. In the example shown, N photodiodes provide respective signals to N resonant amplifiers 145 and a 2N-channel ADC 150. However, the number of photodiode outputs, the number of resonant amplifiers, and the number of channels on the ADC can all differ from each other.

A plurality of resonant amplifiers 145 correspond to respective optical detectors, e.g., in photodiode array 140. In this example, array 140 includes N detectors, and N resonant amplifiers 145 are provided. Each resonant amplifier 145 is operative to amplify portion(s) of the respective electrical signal having a selected temporal frequency (e.g., having a temporal frequency in a selected range) and to attenuate portion(s) of the respective electrical signal not having the selected temporal frequency (e.g., outside the range).

Exemplary resonant amplifiers 145 were constructed, each containing first stage 410 and second stage 420. This configuration is referred to herein as a "tuned amplifier" or "TAMP." First stage 410 included LC resonant circuit 413 and preamplifier 416, e.g., a low-noise JFET-based preamplifier. The tested first stages 410 had dimensions of 1.2"×1"×0.25". LC circuit 413 selectively amplifies the SRL signal (the AC output) at the modulation frequency. After preamplification, the AC signal is sent to second stage 420.

Second stage 420 of resonant amplifier 145 (TAMP) includes amplifier 422, bandpass filter 424, and rectifier 426. Amplifier 422 can include a selectable gain amplifier that provides, in an exemplary tested configuration, four selectable amplifications (gain levels), and increases signal level to a few volts. The bandpass filter 424 attenuates low frequency and high frequency noise that may leak through the resonant circuit. The filtered signal is rectified by rectifier 426, e.g., a full-wave precision rectifier, and then sent to the ADC 150 for digitization. The bipolar ADC can be used to digitize the signal without rectifying it.

Resonant amplifier 145 can be constructed more inexpensively than the lock-in amplifier needed in a traditional SRS system, and has improved signal to noise ratio compared to prior schemes. A single TAMP was constructed, then a TAMP array containing 8 independent resonant amplifier circuits 145 (N=8) was constructed. A TAMP array containing 16 independent resonant amplifier circuits 145 (N=16) was also constructed.

First stage 410 and second stage 420 can be packaged together or separately. For example, in FIG. 2, array 240 includes the first stages 410 of each of the resonant amplifiers 145. Array 246 includes the second stages 420 of those resonant amplifiers 145. Each TAMP (resonant amplifier 145) include both first stage 410 and second stage 420. The first and second stages 410, 420 can be connected by any suitable way of conveying analog signals.

In various aspects, the TAMPs are bandpass filters operating in the temporal-frequency domain, e.g., to pass signals around the 2.1 MHz temporal modulation of a Stokes beam. The TAMPs pass electrical signals from optical sensors (e.g., photodiodes) regardless of the wavelength of light that caused the photodiode to produce that electrical signal.

Figure 5:
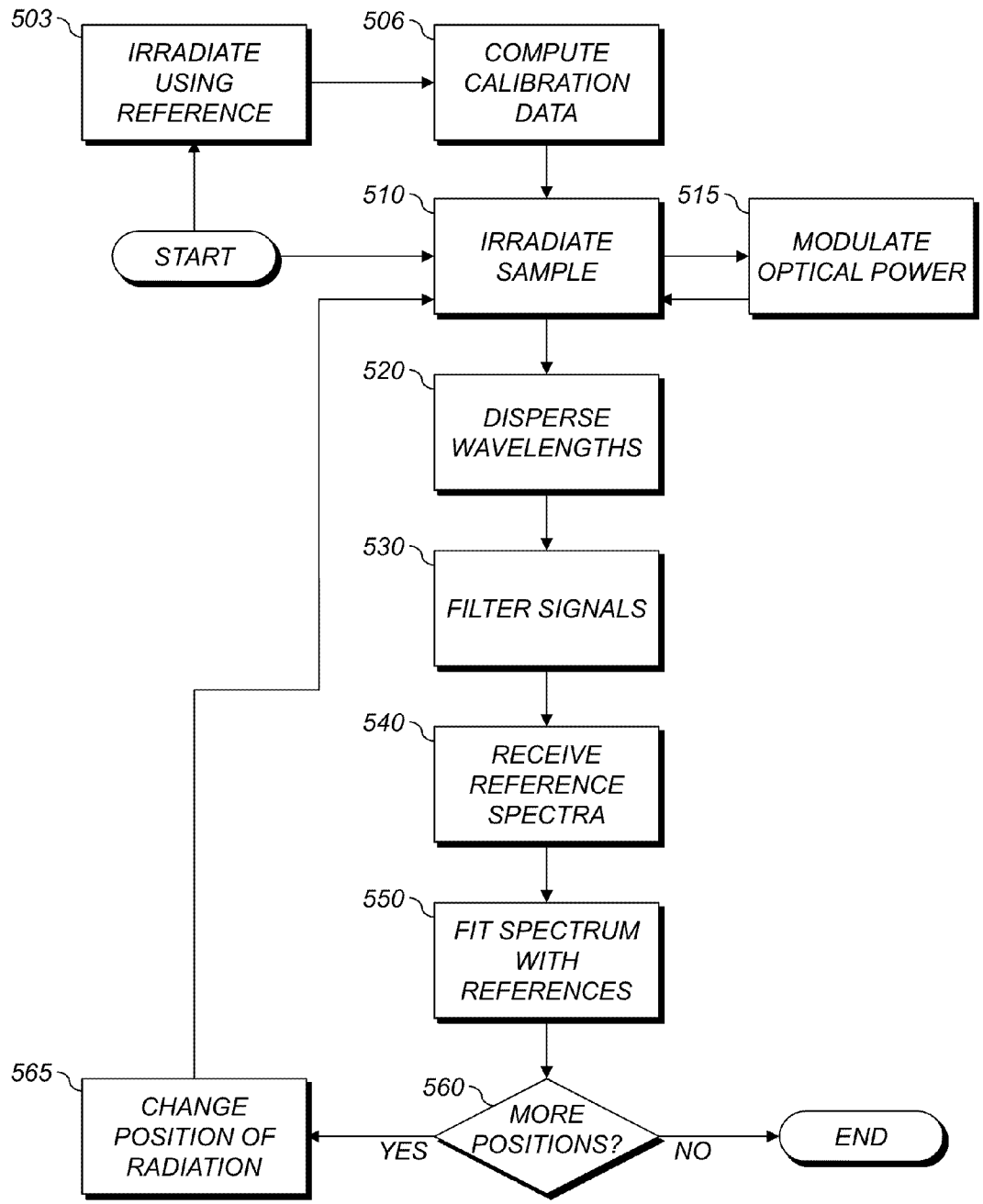
FIG. 5 shows a flowchart illustrating an exemplary method for analyzing constituents of a sample.

FIG. 5 shows a flowchart illustrating an exemplary method for analyzing constituents of a sample. The steps can be performed in any order except when otherwise specified, or when data from an earlier step is used in a later step. In at least one example, processing begins with step 510, or with step 503. For clarity of explanation, reference is herein made to various components shown in FIGS. 1-4 that can carry out or participate in the steps of the exemplary method. It should be noted, however, that other components can be used; that is, exemplary method(s) shown in FIG. 5 are not limited to being carried out by the identified components.

In step 503, before irradiating step 510, optical detectors in a plurality of optical detectors are illuminated with a reference spectrum, e.g., the laser as measured by a spectrometer. This is discussed below with reference to FIG. 8B. In subsequent step 506, respective calibration data for each of the plurality of optical detectors are automatically computed, e.g., using processor 186. Step 510 is next.

In step 510, the sample 101 is contemporaneously (e.g., simultaneously) irradiated with incident radiation including narrowband light and broadband light. As noted above, the term "light" does not restrict the incident radiation to the human-visible wavelengths.

In step 515, while irradiating the sample, the optical power of the narrowband light or the broadband light (or both) is (are) modulated at a selected temporal frequency. For example, the narrowband Stokes beam 112 (FIG. 1) can be modulated. The light irradiates or otherwise interacts with sample 101 to produce resultant light. Step 520 is next.

In step 520, wavelengths of resultant light from the sample are dispersed across the plurality of optical detectors. Step 530 is next. In at least one aspect, the modulating step 515 includes modulating the optical power of the narrowband light, and the dispersing step 520 includes dispersing wavelengths of the broadband resultant light across the plurality of optical detectors.

In step 530, respective signals from the optical detectors are filtered to provide a spectrum dataset of the sample. This filtering can be performed electronically. The spectrum data include bandpass signals corresponding to the selected temporal frequency. In at least one aspect, the filtering step 530 includes passing the respective signals from the optical detectors through respective passive resonant bandpass filter circuits. As described above with reference to FIG. 4, the signal from each optical detector is filtered ("AC" in FIG. 4) in the time domain to retain substantially only components exhibiting frequency content at the selected temporal frequency. In aspects using calibration step 506, filtering step 530 can further include applying the respective calibration data to the respective signals from the optical detectors. Step 530 can be followed by step 540.

In step 540, a plurality of reference spectra are received for respective ones of the constituents. Reference spectra can be received for constituents known to be present in the sample or for constituents for which it is desired to determine whether or not they are present in the sample, or to what extent they are present in the sample. Step 540 can also include, e.g., performing a principal-components analysis. Step 550 is next.

In step 550, a combination of the reference spectra is mathematically fit to the spectrum data of the sample, so that respective fitting coefficients for the reference spectra represent the contributions of respective constituents to the sample. This can be done, e.g., by executing a multivariate curve resolution (MCR) algorithm using the processor 186. Step 550 can be followed by decision step 560, discussed below.

MCR analysis of multiplex SRS images can be performed various ways. In at least one aspect, multivariate curve resolution (MCR) and alternative least squares (ALS) fitting are used to decompose the multiplex SRS images into chemical maps of sample 101. MCR is a bilinear model, capable of decomposing a measured spectral data set D into concentration profiles and spectra of chemical components, represented by matrices C and $S^T$:

$$D = C \cdot S^T + E. \qquad (2)$$

("$X^T$" represents the transpose of matrix.) E is the residual matrix or experimental error. The input to MCR is the dataset D (the measured signals from the optical detectors) and the reference spectra of each component (from step 540). S contains the output spectra of all fitted components. The output concentration of a chemical component at each pixel can be expressed as percentage relative to the intensity of the MCR optimized spectrum. Given an initial estimate of pure spectra either from principal component analysis or prior knowledge (e.g., reference spectra received in step 540), an alternating least squares algorithm can calculates C and S iteratively until the results fit the data matrix D and satisfy a mathematical-optimality criterion. Non-negativity on both concentration and spectra profiles can be applied as a constraint during the alternating least squares iteration.

In order to reduce ambiguity associated with MCR decomposition, a data augmentation matrix composed of repeating reference spectra, if needed, can be added to the spectral dataset D. The enhanced weight on pure reference spectra permits the MCR algorithm to selectively recover concentration profiles for corresponding Raman bands. An experiment was performed to test this. For tissue penetration data, pure DMSO spectrum and lipid spectrum were provided as initial estimations (reference spectra) for MCR analysis. A data augmentation matrix including reference spectra of DMSO and lipid was added to the spectral dataset in order to reduce ambiguity. For analysis of aqueous solutions of DMSO, a data augmentation matrix composed of reference spectra of DMSO was added to the spectral dataset in order to reduce MCR's ambiguity. A non-negativity constraint was used during the iterations.

In decision step 560, it is determined whether the position of the incident radiation with respect to the sample 101 should be changed. If so, step 565 is next. This can be used, e.g., for laser scanning aspects that successively irradiate a sample 101 is from several angles, or different portions of the sample 101 are successively irradiated. In an example, the laser scans across the sample 101 to provide measurements at each of a plurality of defined pixel areas on sample 101.

In step 565, the position of the incident radiation with respect to the sample is changed. Step 510 is next. In this way, the irradiating, modulating, dispersing, and filtering steps are repeated, so that respective spectrum datasets are provided for each of a plurality of positions of the incident radiation.

Figure 6:
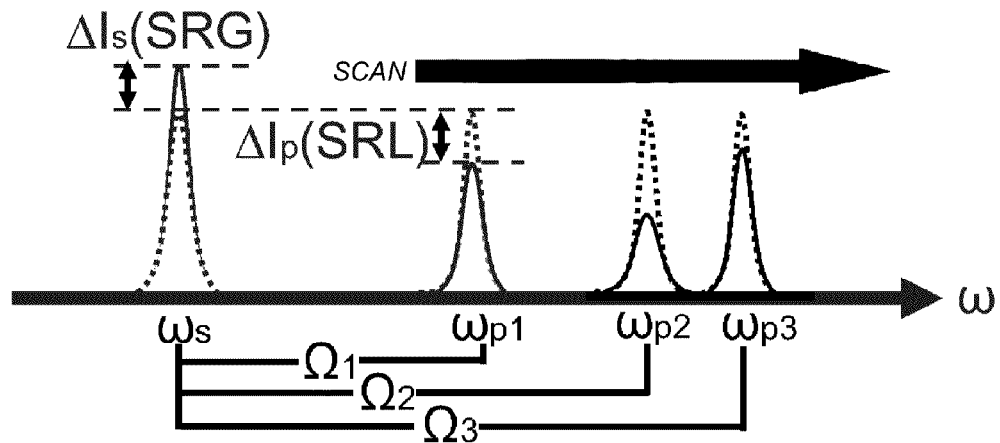
FIG. 6 shows an example of SRS measurement of a sample according to prior schemes.
Figure 7:
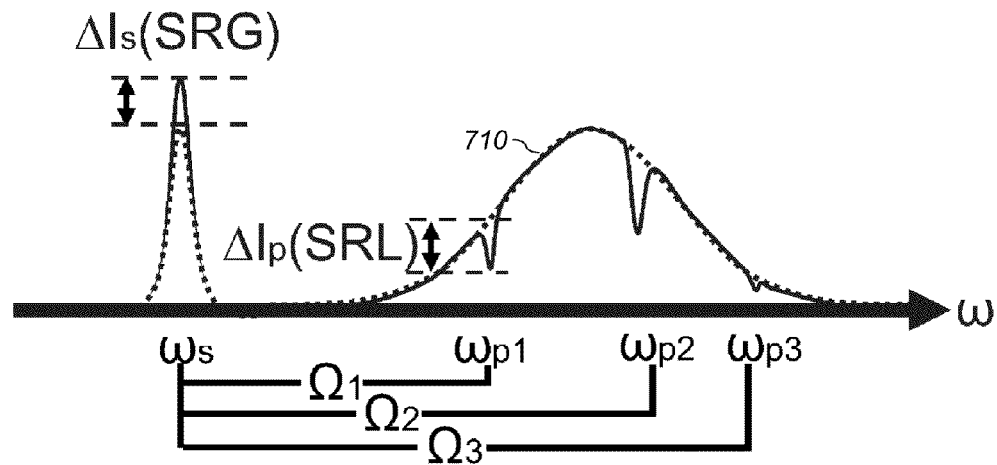
FIG. 7 shows an example of SRL spectra produced using narrowband Stokes and broadband pump excitation according to various aspects.

FIG. 7 shows an example of SRL spectra produced using narrowband $\omega_S$ and broadband $\omega_p$ excitation. Dotted lines show radiation before interaction with the sample; dashed lines show radiation after interaction with the sample. Unlike FIG. 6, discussed above, the pump beam provides a wide range of wavelengths, as shown by peak 710. Accordingly, SRL is evident as notches in peak 710. Peak 710 (solid line), with SRL notches, is dispersed over the optical detectors so that the notches can be measured.

In various aspects, the pump beam is narrowband and the Stokes beam is broadband. SRL is observed in the pump beam. SRG is observed in the dispersed, measured Stokes wavelength range. CARS microscopy can also or alternatively be performed using this technique, as the CARS signal appears at the anti-Stokes frequencies corresponding to the Stokes frequencies (SRG peaks) observed in the measured resultant radiation. A narrowband pump beam and a broadband Stokes beam provide broadband SRG and CARS spectra simultaneously.

Figure 8A:
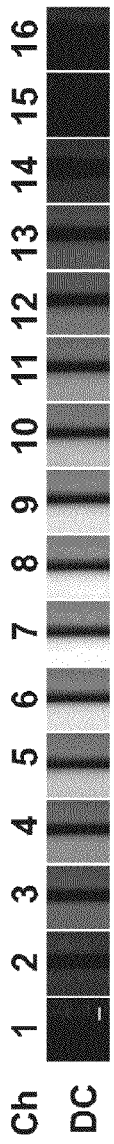
FIGS. 8A and 8B show experimental data of calibration of the optical detectors according to various aspects, FIG. 8A including a graphical representation of micrographs.
Figure 8B:
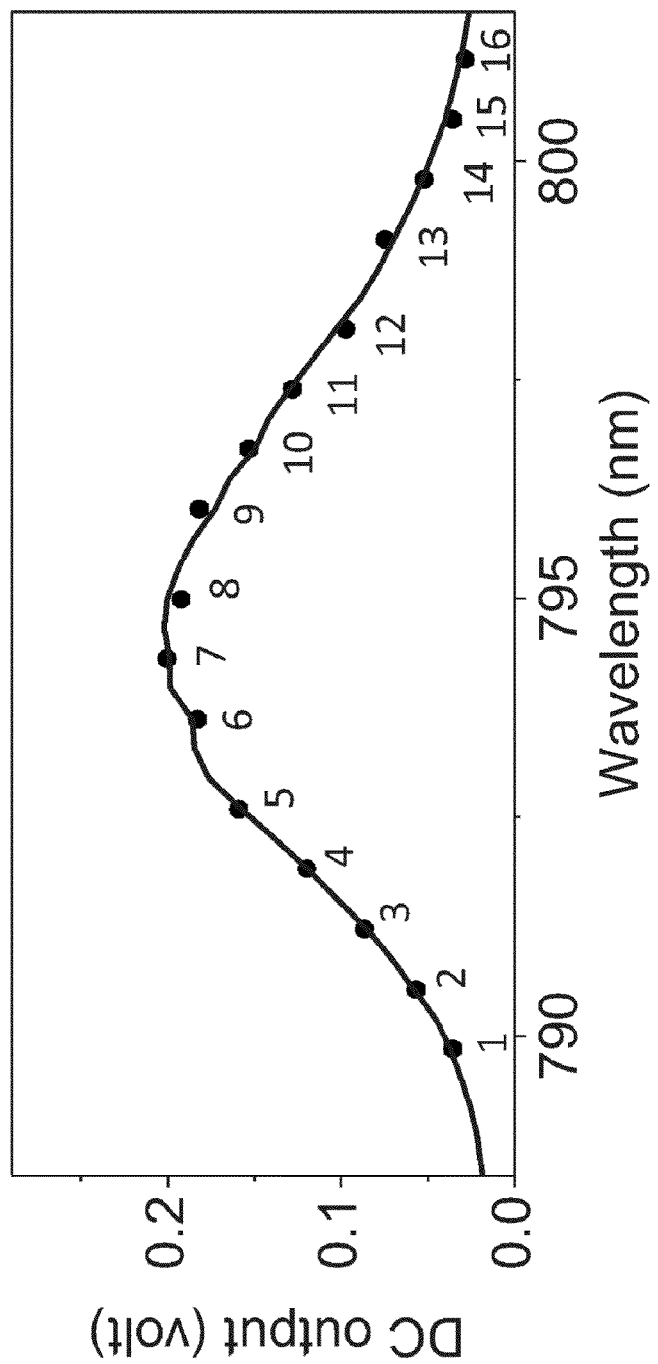

FIGS. 8A and 8B show experimental data of calibration of the optical detectors according to various aspects. To collect these data, a hybrid scanning microscope was used as described above with 16 optical detectors (each identified as "ch" or channel 1-16). Accordingly, each optical detector captured one data point for each pixel in a grid rasterized over the sample 101. The data points for each optical detector for one pixel can be combined to produce a spectrum. Alternatively, the data points for each pixel for one optical detector can be combined to produce an image corresponding to a specific detected wavelength.

FIG. 8A is a graphical representation of the 16 images for the respective optical detectors. Each image combines the readings from that detector for each pixel measured. The tested sample 101 was an interface with pure dimethyl sulfoxide (DMSO) solution on the left and air on the right.

FIG. 8B shows calibration data and experimental data corresponding to the laser. Points indicate the DC output from each channel. The DC output measures the intensity of the local oscillator (e.g., resultant radiation beam 139, FIG. 1) on each spectral channel. The line shows the spectrum of the pump laser measured independently by a spectrometer. The 16-channel DC outputs were mathematically fit to the spectrum to perform spectral calibration. The dispersion was determined to be 0.4 nm per mm on the photodiode array, so the 16 tested odd-numbered channels covered a range of ~11.5 nm, as shown. The spectrum shown is the measurement from a single pixel, as is the spectrum shown in FIG. 9B, discussed below.

FIGS. 9A and 9B show experimental data of determining Raman shifts using the system calibrated as described above with reference to FIGS. 8A and 8B. Based on the spectral calibration and the wavelength of the Stokes beam fixed at 1040 nm, the Raman shifts were calculated. The AC signal gain for each channel were measured by introducing small intensity modulation in the pump beam and fitting the AC profile to DC profile. The gain profile and the DC profile were combined to calibrate the raw Raman-shift data.

FIG. 9A is a graphical representation of the 16 images for the AC signals from the respective optical detectors. Higher intensity of SRL is shown as a brighter shade. The AC signal of each channel was calibrated by the DC amplitude and the gain. As can be seen, channel 5 has a bright left (DMSO) half, corresponding to the high magnitude of SRL at the corresponding Raman shift.

FIG. 9B shows (dots) the calibrated AC signal readings. The solid line shows the polarized Raman spectrum for DMSO. As can be seen, the measurement had acceptable accuracy. The Raman shift corresponds here to the energy difference between pump and Stokes wavelength and is calculated as Raman shift $[cm^{-1}]=10^7/(pump\ wavelength)-10^7/(Stokes\ wavelength)$.

FIGS. 10A, 10B, 11A, 11B, and 12 show experimental data of SRS imaging. Various aspects of parallel detection herein advantageously provide a speed of acquiring a spectrum at 30 µs time scale, or over 30,000 spectra per second. For imaging, this scheme avoids spectral profile distortion induced by sample movement, thus enabling observation of target molecules in a highly dynamic system. To demonstrate in situ mapping of dynamic changes of target molecules, DMSO was applied to intact mouse ear and DMSO penetration into the lipid-abundant layer located ~50 µm beneath the skin surface was monitored. Every three minutes, one spectroscopic SRL image was acquired at the speed of 3 s per frame of 200×200 pixels. Importantly, although the C—H Raman spectra of DMSO and lipid are completely overlapped, spectroscopic SRS imaging, followed by employing MCR analysis as described above, permitted determining concentration maps of lipids and DMSO over time.

Figure 10A:
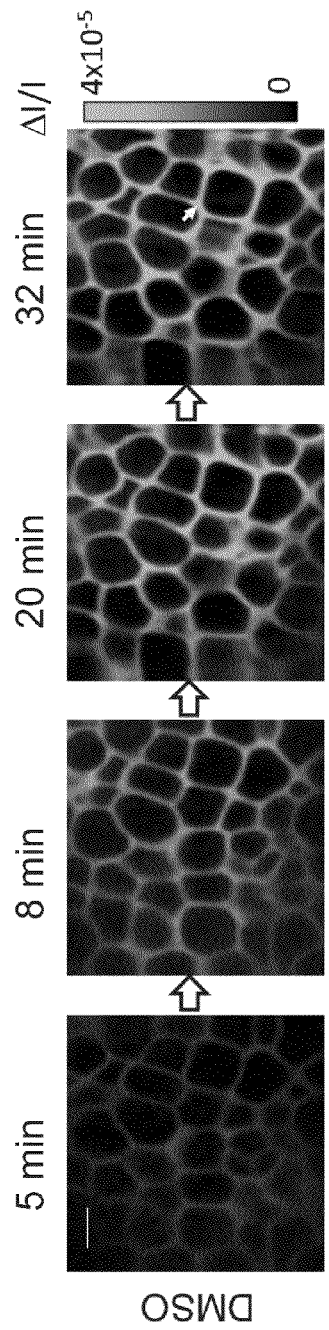
FIGS. 10A, 10B, 11A, 11B, and 12 show experimental data of SRS imaging, FIGS. 10A and 10B including graphical representations of micrographs.
Figure 10B:
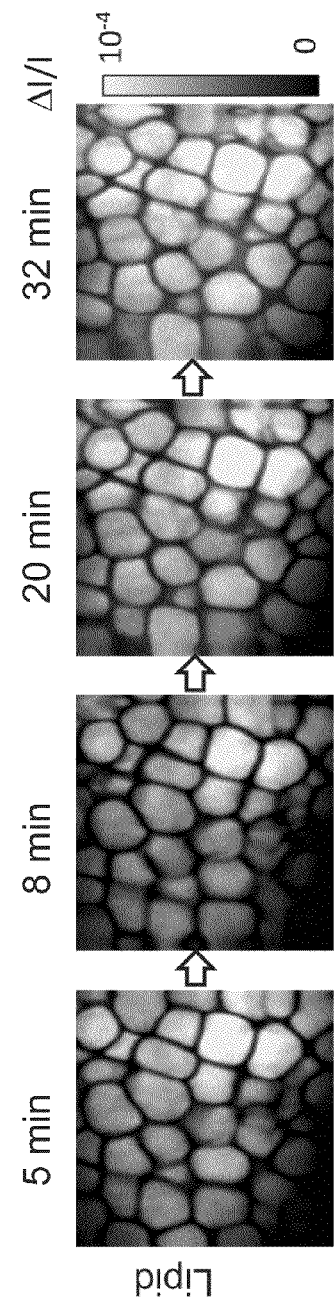

FIG. 10A shows a graphical representation of the DMSO concentration maps, and FIG. 10B a graphical representation of the lipid concentration maps, at 5, 8, 20, and 32 minutes after DMSO application. Very small amounts of DMSO molecules penetrated into the adipose tissue in the first 5 min. After 30 min, inter-cell distribution of DMSO was observed. The structure of the fat cells remained intact. The scale bar in the 5-minute image in FIG. 10A is 20 µm. The arrow near the center of the 32-minute image in FIG. 10A indicates the location at which concentrations were measured for FIG. 12, discussed below.

Figure 11A:
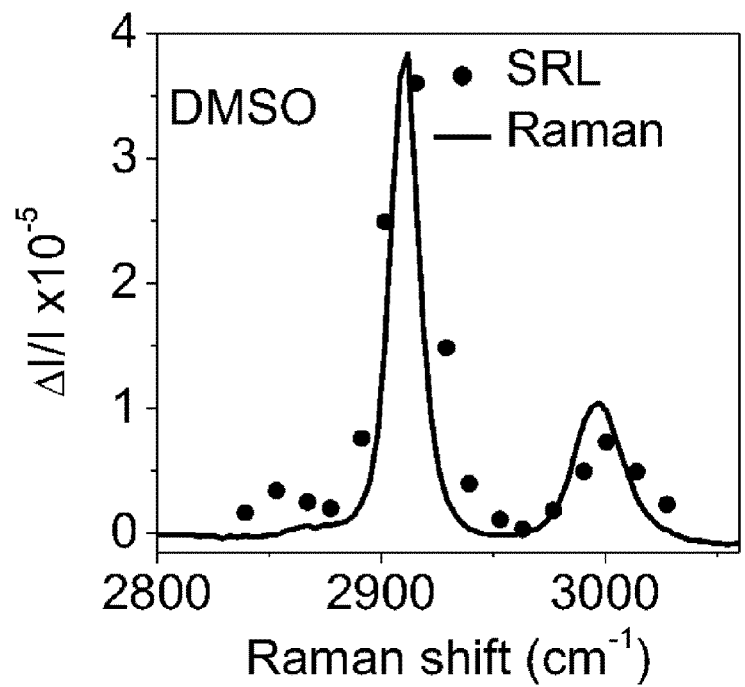
Figure 11B:
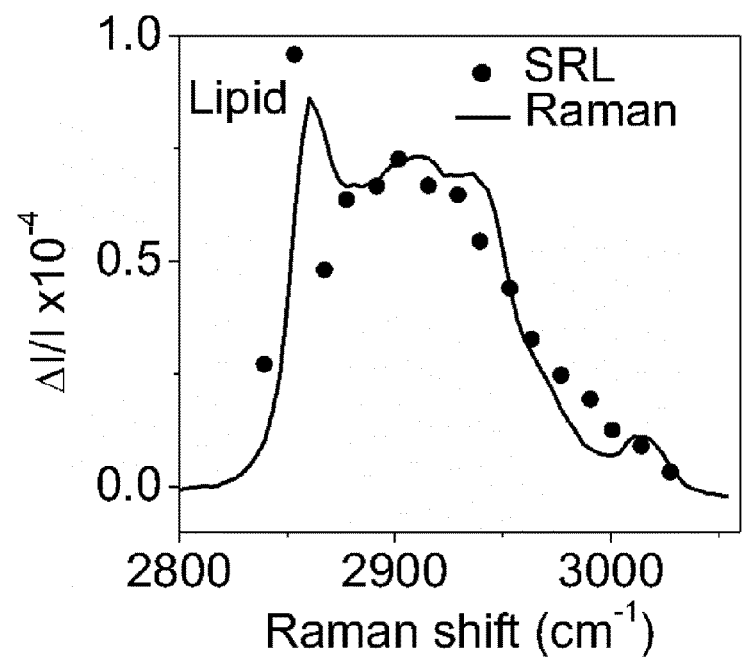

FIGS. 11A and 11B show single-pixel MCR output and corresponding Raman spectra for DMSO and lipid, respectively. These data show effective determination of the components.

Figure 12:
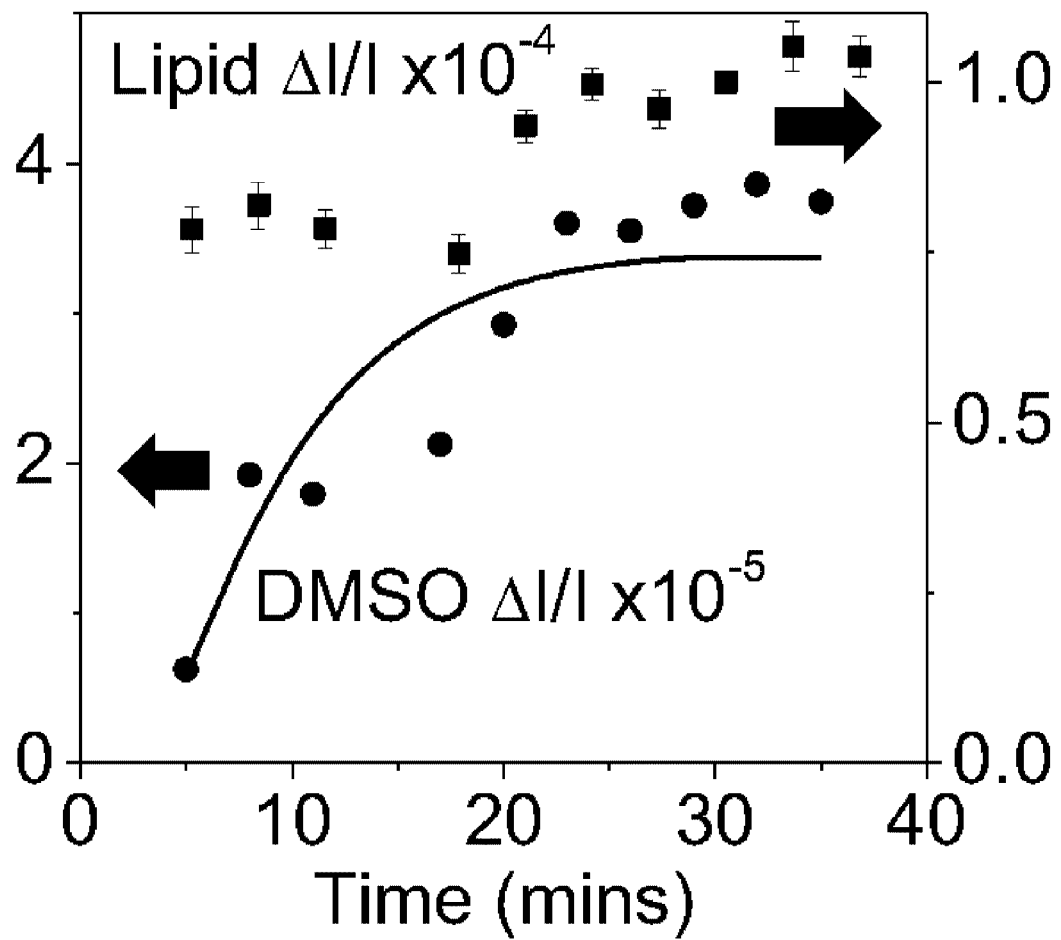

FIG. 12 shows time-lapsed intensity of DMSO and lipid measured in the inter-cell region. The temporal dynamics of DMSO (circles) and lipid (squares) concentrations are shown. The curve represents fitting by a diffusion model. The time-lapsed intensities, which were proportional to the concentration of DMSO in the focal volume, can be well fitted with a diffusion equation. The lipid maps (FIG. 10B) showed the morphology of fat cells, where the intensity of lipids slightly increased overtime. This increase can be due to the penetration of DMSO, which served as a moderate tissue clearance agent. Collectively, these data demonstrate the capability of multiplex SRS microscopy for real-time, in situ, and chemically selective imaging for fast dynamic processes.

FIGS. 13, 14, and 15A-15C show experimental data of multiplex SRS imaging of living Chinese hamster ovary (CHO) cells. Scale bars throughout are 20 µm.

FIG. 13 shows a graphical representation of an SRL image captured using the channel 6 optical detector. Signals are contributed by overlapping Raman bands including $CH_2$ and $CH_3$. The image of 200×200 pixels was acquired in 3.0 s, at the speed of 30 µs per pixel.

FIG. 14 shows MCR output spectra of $CH_2$, $CH_3$ and OH. Channel 6 is marked. Single cell analysis is shown by the multiplex SRS imaging of living Chinese hamster ovary cells in the C—H vibration region of Raman shifts from 2790 to 3060 $cm^{-1}$.

FIGS. 15A-15C show graphical representations of concentration maps of $CH_2$, $CH_3$ and OH, respectively. These correspond to distributions of lipid, protein, and water, respectively. These were produced using MCR analysis to decompose the spectroscopic image into the concentration maps. As shown, the $CH_2$ map (FIG. 15A) is largely contributed by lipid bodies stored inside the cells. The $CH_3$ map (FIG. 15B) is largely contributed by proteins that are ubiquitous inside the cells. The map of $H_2O$ (FIG. 15C) dominates the entire field view except the lipid bodies that contain little water content. These data indicate that aspects described herein enable using spectroscopic SRS imaging of biochemistry in live cells.

Figure 16A:
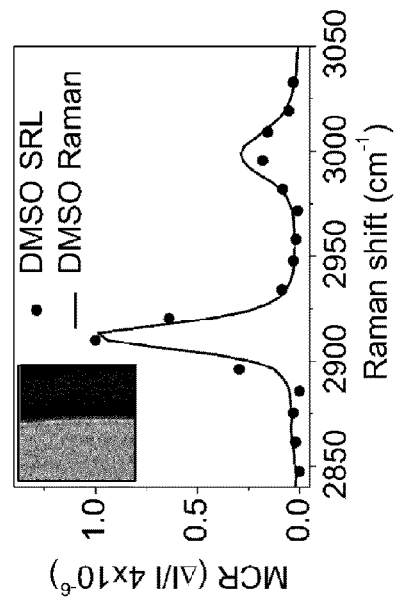
FIGS. 16A-16D show experimental data of spectroscopic SRL imaging and MCR analysis of diluted DMSO aqueous solutions, the insets of FIGS. 16A-16C including graphical representations of micrographs.
Figure 16B:
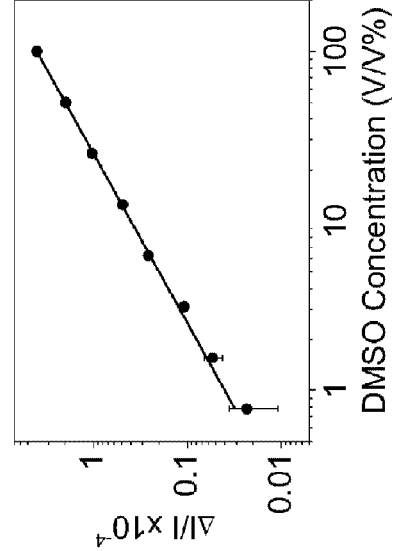
Figure 16C:
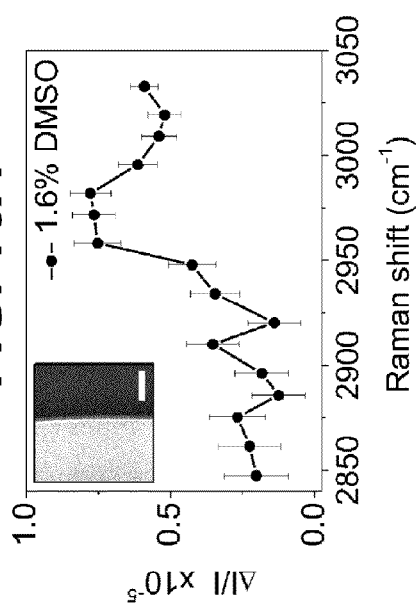

FIGS. 16A-16D show experimental data of spectroscopic SRL imaging and MCR analysis of diluted DMSO aqueous solutions at various concentrations. These data show that spectral detection techniques herein can effectively extract the signal of target molecules from solvent background in SRS microscopy. DMSO spectrum and water spectrum were used as initial estimations for MCR analysis. The insets of FIGS. 16A-16C are graphical representations of respective SRS images.

Figure 16D:
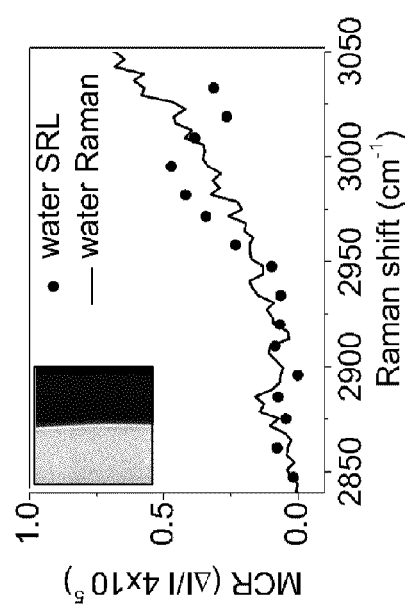

FIG. 16A shows an SRL spectrum of a 1.6% DMSO solution. FIG. 16B shows MCR output of DMSO concentration map and the corresponding spectrum. FIG. 16C shows MCR output of water concentration map and the corresponding spectrum. FIG. 16D shows dependence of the SRS signal (represented as modulation depth $\Delta I/I$) on DMSO concentration. As shown, the spectroscopic image for 1.6% DMSO aqueous solution was successfully decomposed into two components. The water solvent presented dominated signal over DMSO. Nevertheless, MCR analysis of the multiplex SRL image was able to extract the SRS signal of DMSO ($\Delta I/I=4\times10^{-6}$) from the solvent background. Linearity of the parallel detection scheme was demonstrated by imaging aqueous solutions of DMSO at various concentrations (FIG. 16D). These data demonstrate the effectiveness of the TAMP array approach for spectral imaging.

FIGS. 17-20 show experimental data of characterization and performance tuning of a 16-channel TAMP array. Due to the tolerance (e.g., 1% to 10%) of electronics elements such as capacitors and inductors in the LC circuit 413 or other components of resonant amplifier 145, the resonant amplifiers 145 may exhibit different resonant frequencies which potentially can degrade the signal-to-noise ratio of the output. In various aspects, each resonant amplifier 145 circuit is designed as a module that can be readily detached from other components, e.g., optical detectors 140. This permits adjustment of gain and resonance frequency of individual resonant amplifiers 145.

Figure 17:
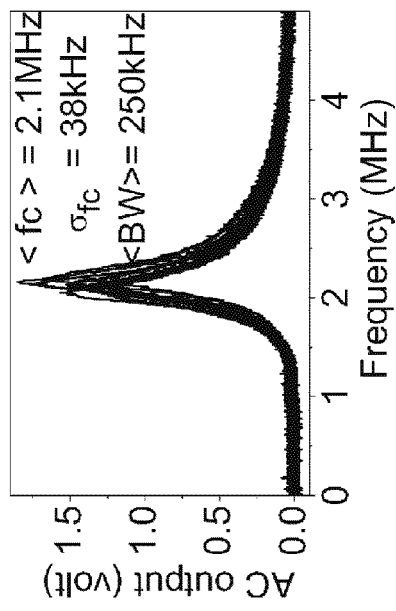

2.1 MHz-resonant TAMPs were constructed and the frequency response of each was measured by sweeping the temporal frequency of modulation from 0 Hz to 5 MHz. FIG. 17 shows the corresponding temporal frequency outputs from all measured TAMPs superimposed. $\langle f_c \rangle$ is average central frequency. $\sigma_{fc}$ is the standard deviation of central frequency. BW is the −3 dB bandwidth of the frequency response in the temporal-frequency domain. The standard deviation of central frequency is one order of magnitude smaller than the bandwidth.

The resonant frequency is centered at 2.1 MHz, with 38 kHz standard deviation. The average temporal bandwidth (at −3 dB) was 250 kHz, resulting in a Q factor close to 10. Because the standard deviation of the resonant frequency was smaller than the bandwidth by nearly one order of magnitude, the TAMPs were determined to be qualified for parallel detection use.

Figure 18:
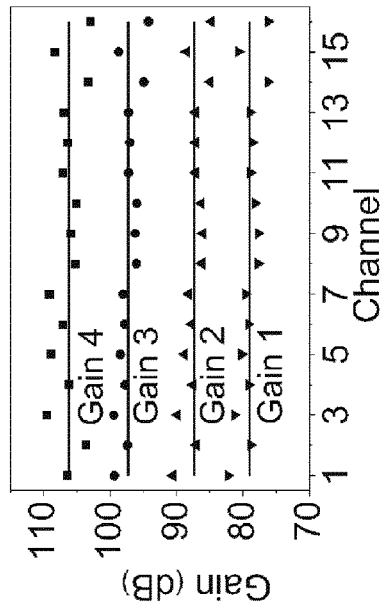
FIGS. 17-20 show experimental data of characterization and performance tuning of a 16-channel TAMP array.

The electronics tolerance also caused variation of the gains between TAMPs. FIG. 18 shows measured gains of 16 TAMPs (channels) under four different gain settings ("Gain 1" through "Gain 4"). The four gain settings provided approximately 78, 88, 98 and 108 dB amplifications, respectively, enhancing the signal level from several micro-volts to a few volts. The deviation between channels was around 4 dB. To compensate this gain deviation, the AC output was calibrated by the gain of each channel. After gain calibration, correct SRL spectra were collected by the parallel detection scheme.

Figure 19:
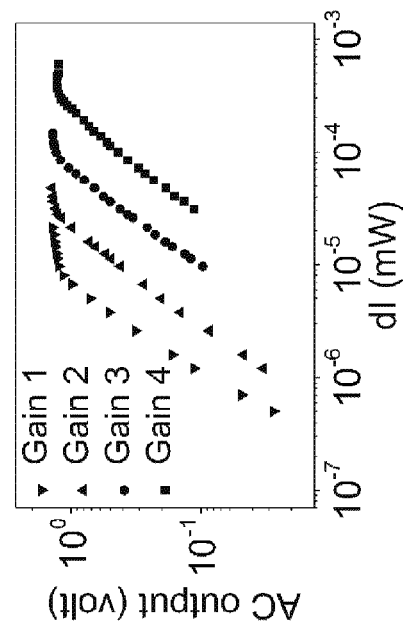

FIG. 19 shows the measured power dependence of channel 5. The AC output is saturated at 1.1 volt, and the four gain settings provide linear power dependence before saturation. To perform this test of linearity of the TAMP array, the laser power dependence of the SRS signal (i.e., AC output) was measured. An 800-nm beam was modulated at $\Delta I/I=10^{-4}$ level and each channel was illuminated separately in order to mimic the SRS signal. By tuning the laser power on each single channel, the linearity of the TAMP array at each gain setting was measured. The AC output saturated at ~1.0 volt, below which the output was linear with local oscillator power in the range of 2 µW to 1.3 mW. Such dynamic range can provide effective imaging. All 16 channels had the same behavior of linear power dependence.

Figure 20:
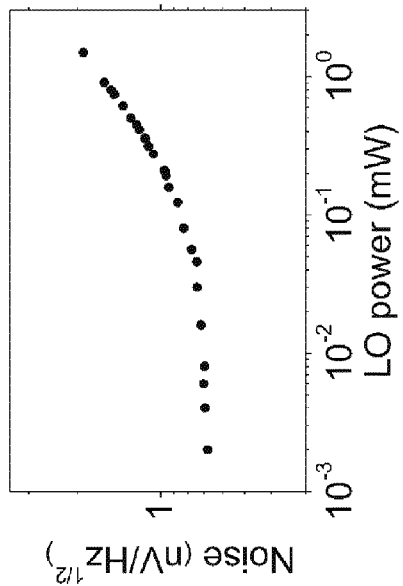

FIG. 20 shows the measured noise level of channel 5. The noise level, calculated as the standard deviation of the pixel intensity with illumination of pump beam, is close to theoretic shot noise at 0.3 mW pump power. To perform this test to identify sources of noise in measurements, the local oscillator (incident radiation) power was increased and the noise level of each channel was measured. The noise level of channel 5 as a function of local oscillator power is shown in FIG. 20. Below 0.1 mW, the noise was dominated by the electronics noise which is close to 0.07 µV/√Hz. In the range from 0.1 to 1.0 mW, the noise gradually approached the theoretic shot noise level. In typical applications, the power of the dispersed local oscillator ranged from 0.05 to 1.0 mW depending on the channel position. Thus, nearly all channels work with shot-noise-limited detection sensitivity.

A tested first-stage TAMP array 410 and photodiode array 140 were integrated into an 8"×8"×5" box that was smaller than a commercial lock-in amplifier. The second stage 420 of the TAMP array and the power supply, connecting to the first-stage TAMP array, were integrated into a 17"×15"×9" box.

In a tested configuration, the resonant frequency of each channel was designed to be centered at 2.1 MHz, with a standard deviation smaller than the bandwidth by one order of magnitude. To compensate the gain deviation, the AC signal was calibrated by the gain of each channel. All tested channels worked with high linearity and shot-noise-limited detection sensitivity.

In various aspects, to calibrate spectroscopic information from a TAMP array (e.g., 32 channels) for quantitative analysis, a spectrum of olive oil extracted using imaging systems described herein can be compared with a Raman spectrum in the C—H region. To determine sensitivity and noise level of an imaging system, aqueous solutions of DMSO can be measured with various DMSO concentrations and laser powers. Imaging can be performed of live cancer cells, PC3, to test extraction of chemical components with high spectral resolution. The sterol C=C, acyl C=C, and amide I bands can be used to generate chemical maps of cholesterol, lipid, protein and nucleic acid, respectively, using an MCR analysis of captured multiplex SRS images.

In various aspects, a high-speed multiplex SRS microscope uses parallel detection with a pixel dwell time of 20 µs and a spectral resolution of 5 cm$^{-1}$. Such a microscope can measure a 100 µm×100 µm are in less than 3 s. Such a microscope can be shot-noise limited as described above with reference to FIG. 20. Such a microscope can have a linear SRS intensity dependence on DMSO concentrations, and a detection sensitivity of 0.5% DMSO.

Figure 21C:
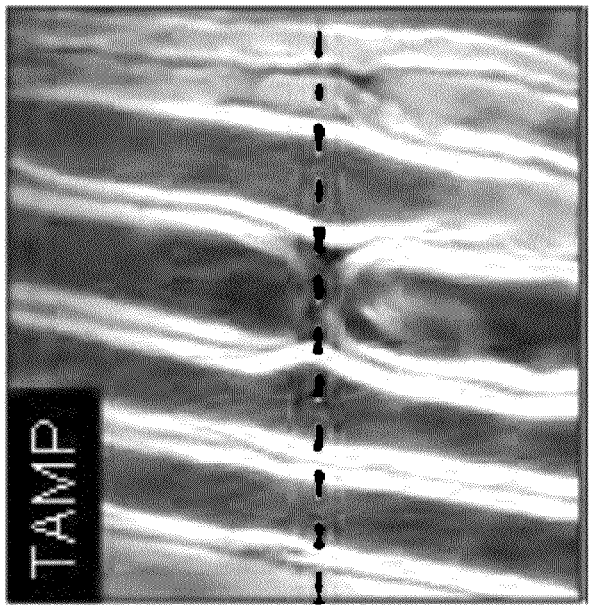
FIGS. 21C-21D show experimental data of an inventive system according to various aspects, FIGS. 21A and 21C including graphical representations of micrographs.
Figure 21D:
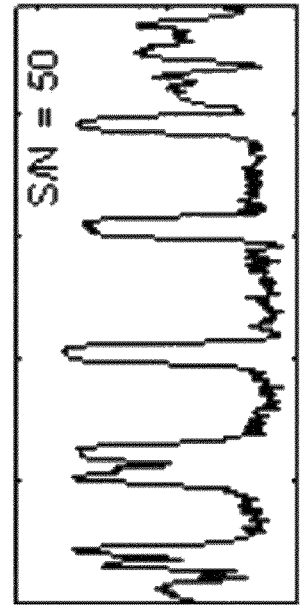
Figure 21A:
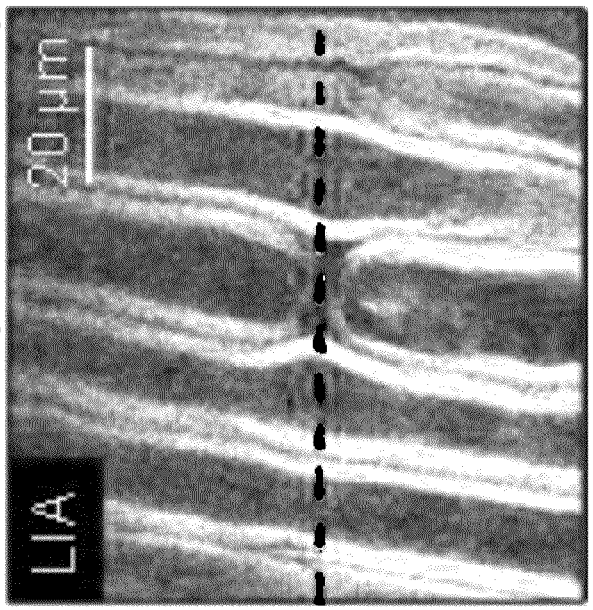
FIGS. 21A-21B show experimental data of a comparative system.
Figure 21B:
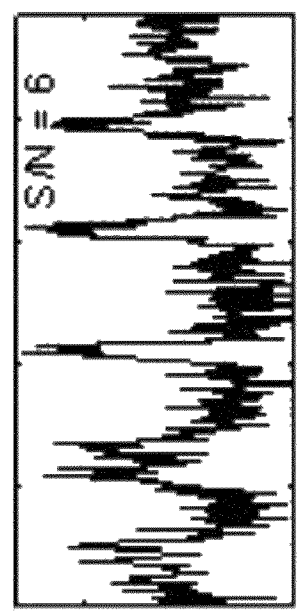

FIGS. 21A-21B show experimental data of a comparative system, and FIGS. 21C-21D show experimental data of an inventive system described herein demonstrating advantages of various aspects. These figures show ex vivo epi-detected SRS data of axonal myelin. FIG. 21A shows a graphical representation of an SRS image captured using a comparative system having a lock-in amplifier (LIA). FIG. 21B shows an intensity profile along the black dashed line horizontally superimposed over the image in FIG. 21A. The signal-to-noise (S/N) ratio for this comparative profile is 6. FIG. 21C shows a graphical representation of a corresponding SRS image captured using an inventive tuned amplifier. FIG. 21D shows an intensity profile along the black dashed line in FIG. 21C. The S/N ratio for this inventive profile is 50, 8.3× higher than the comparative lock-in amplifier.

FIGS. 22A-22G show experimental data of SRS imaging of live pancreatic cancer MIAPACA-2 cells. An 8-channel photodiode and TAMP array was used to simultaneously acquire 8 AC signals (SRL spectral profile) and 8 DC signals (pump beam spectral profile). By tuning the beating frequency to the C—H vibration region and by multivariate analysis (MCR) of the 8-channel SRS signals, chemical maps of $CH_2$, $CH_3$, and OH groups, which correspond to the distribution of lipid, protein and water, respectively, were obtained. These data demonstrate effective measurement of live cells.

Figure 22A:
FIGS. 22A-22G show experimental data of SRS imaging of live pancreatic cancer MIAPACA-2 cells, FIGS. 22A-22C and 22E-22G including graphical representations of micrographs.
Figure 22B:
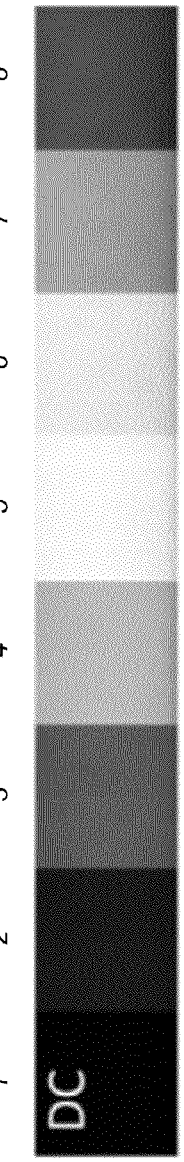
Figure 22C:
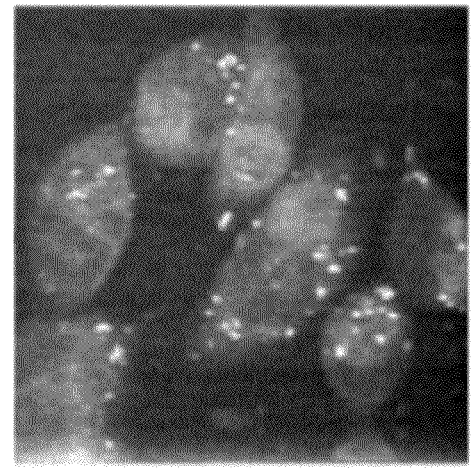

FIG. 22A is a graphical representation of the AC images captured for the 8 channels, labeled with channel numbers 1-8. FIG. 22B is a graphical representation of the DC images captured, which are substantially flat fields (e.g., which have no sharp features) since the DC signal is generated by the local oscillator after filtering and therefore does not provide information corresponding to the SRS signal. FIG. 22C is a graphical representation of the averaged AC image.

Figure 22D:
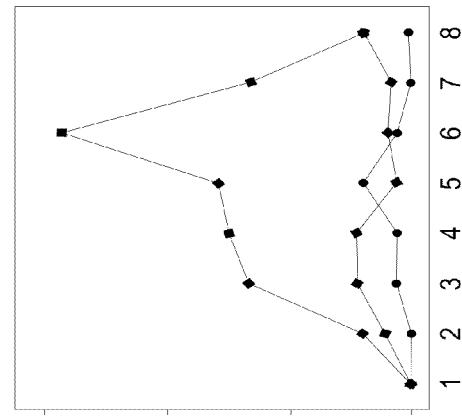

FIG. 22D shows the MCR results for one pixel, for all eight channels.

Figure 22G:
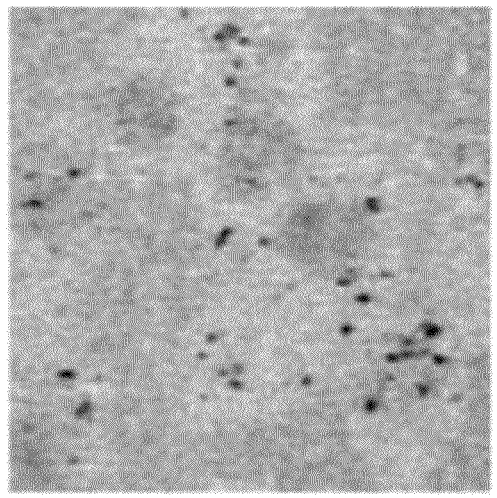
Figure 22F:
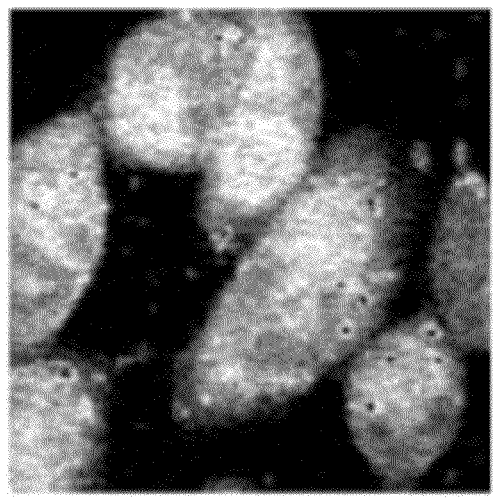
Figure 22E:
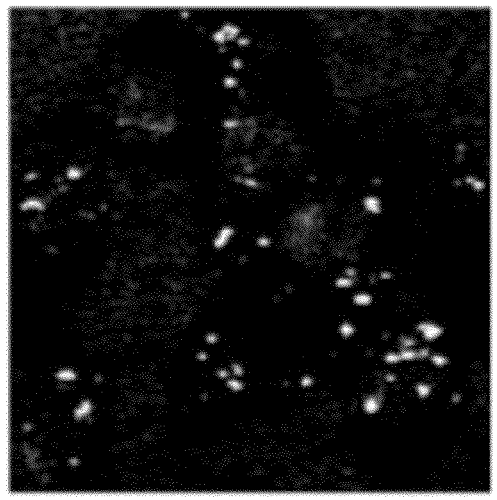

FIGS. 22E-22G are graphical representations of the separated SRS images for $CH_2$ (lipid), $CH_3$ (protein), and OH (water), respectively.

Herein is described a platform for acquisition of Raman spectrum at microsecond time scale and spectroscopic imaging of biological processes in living cells and intact tissues. Data is shown herein for 8- and 16-channel arrays. In various aspects, more than 16 channels are used, e.g., 128 channels. A 128-channel or other array can be designed to cover the entire fingerprint region (e.g., broadband pump radiation wavelength band) using a suitable broadband laser source. Moreover, the pixel dwell time can be further reduced by using a faster ADC 150. Various aspects herein permit using Raman spectroscopy, a technique mainly used for point measurement in prior schemes, for in situ analysis of target molecules in their natural environment.

Specifically, the data based on the 8-channel TAMP array show that a 32-channel multiplex SRS microscope using parallel detection can be provided. In a living cell system, protein, lipid and water can be extracted individually for future quantitative analysis. SRS signals with 180 $cm^{-1}$ spectral bandwidth can be used, at a spectral resolution of 23 $cm^{-1}$ using an 8-channel multiplex microscope, or higher resolution using larger arrays or wavelength tuning (the latter providing, e.g., 10 $cm^{-1}$ spectral resolution). Spectral resolution can be increased to 5 $cm^{-1}$ by increasing the number of photo-detectors and TAMP circuits. Chemical components such as, for example, DNA and cholesterol can be identified in an intact tissue or single cells. Parallel detection as described herein permits increasing spectral resolution by increasing the number of channels without reducing the pixel dwell time or frame rate. For example, based on the constructed 8-channel TAMP array, a 32-channel array can be provided in an 8"×8"×5" box.

In view of the foregoing, various aspects provide improved sensing of analytes, and specifically more rapid detection of Raman-spectroscopy data. A technical effect is to detect a physical property or characteristic of the analyte by detecting the effect of the analyte on the incident electromagnetic radiation.

Figure 23:
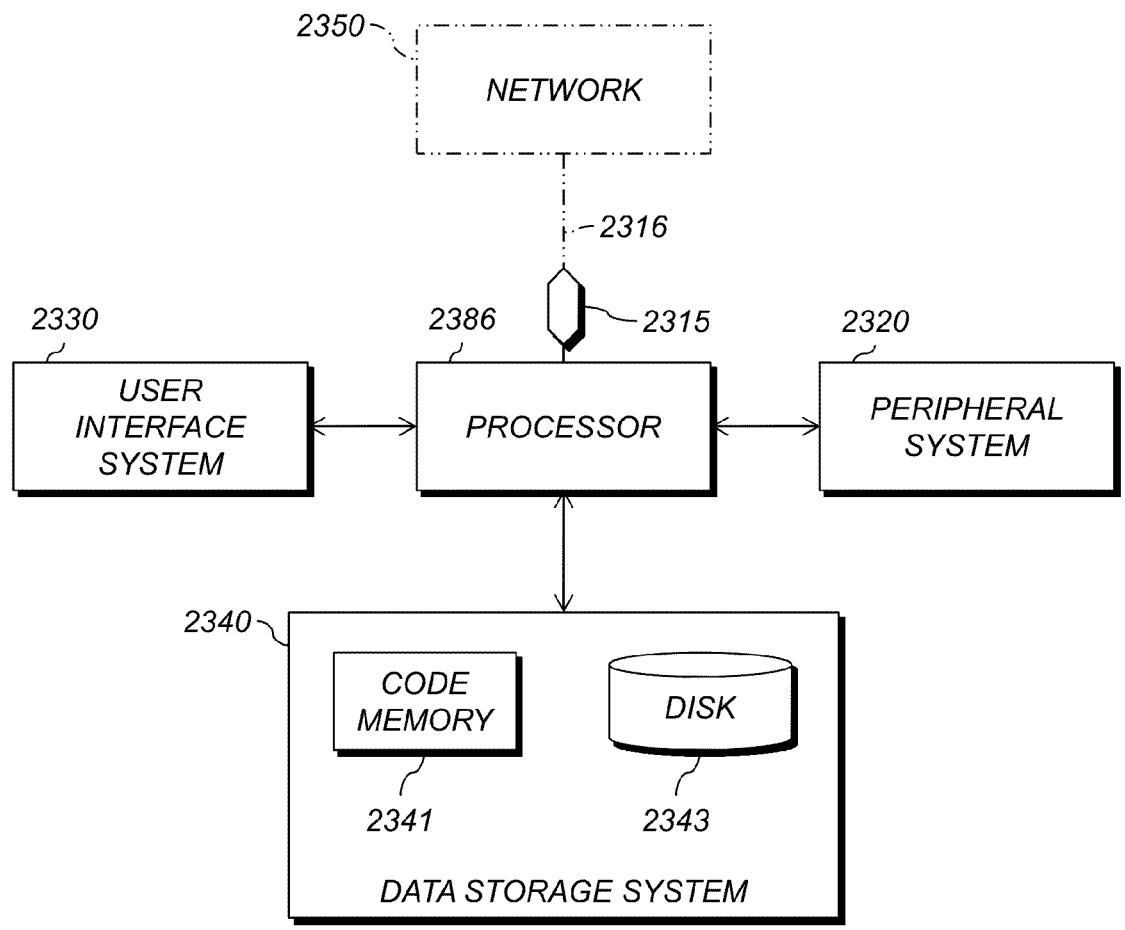
FIG. 23 is a high-level diagram showing the components of a data-processing system.

FIG. 23 is a high-level diagram showing the components of an exemplary data-processing system for analyzing data and performing other analyses described herein, and related components. The system includes a processor 2386, a peripheral system 2320, a user interface system 2330, and a data storage system 2340. The peripheral system 2320, the user interface system 2330 and the data storage system 2340 are communicatively connected to the processor 2386. Processor 2386 can be communicatively connected to network 2350 (shown in phantom), e.g., the Internet or an X.15 network, as discussed below.

The following devices or systems described herein can each include one or more of systems 2386, 2320, 2330, 2340, and can each connect to one or more network(s) 2350: the photodiode array 140 or a controller thereof (e.g., processor 186); the TAMP array; each individual resonant amplifier 145 (e.g., each TAMP); the multichannel ADC 150 or a controller thereof (e.g., processor 186); processor 386 or other computer; or other processing devices described herein. Processor 2386, and other processing devices described herein, can each include one or more microprocessors, microcontrollers, field-programmable gate arrays (FPGAs), application-specific integrated circuits (ASICs), programmable logic devices (PLDs), programmable logic arrays (PLAs), programmable array logic devices (PALs), or digital signal processors (DSPs).

Processor 2386 can implement processes of various aspects described herein, e.g., steps discussed above with reference to FIG. 5. Processor 2386 and related components can be embodied in one or more device(s) for automatically operating on data, e.g., a desktop computer, laptop computer, mainframe computer, personal digital assistant, digital camera, cellular phone, smartphone, or any other device for processing data, managing data, or handling data, whether implemented with electrical, magnetic, optical, biological components, or otherwise.

The phrase "communicatively connected" includes any type of connection, wired or wireless, for communicating data between devices or processors. These devices or processors can be located in physical proximity or not. For example, subsystems such as peripheral system 2320, user interface system 2330, and data storage system 2340 are shown separately from the processor 2386 but can be stored completely or partially within the processor 2386.

The peripheral system 2320 can include one or more devices configured to provide digital content records to the processor 2386. For example, the peripheral system 2320 can include digital still cameras, digital video cameras, cellular phones, or other data processors. The processor 2386, upon receipt of digital content records from a device in the peripheral system 2320, can store such digital content records in the data storage system 2340.

The user interface system 2330 can include a mouse, a keyboard, another computer (connected, e.g., via a network or a null-modem cable), or any device or combination of devices from which data is input to the processor 2386. The user interface system 2330 also can include a display device, a processor-accessible memory, or any device or combination of devices to which data is output by the processor 2386. The user interface system 2330 and the data storage system 2340 can share a processor-accessible memory.

In various aspects, processor 2386 includes or is connected to communication interface 2315 that is coupled via network link 2316 (shown in phantom) to network 2350. For example, communication interface 2315 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link, e.g., WiFi or GSM.

Communication interface 2315 sends and receives electrical, electromagnetic or optical signals that carry digital or analog data streams representing various types of information across network link 2316 to network 2350. Network link 2316 can be connected to network 2350 via a switch, gateway, hub, router, or other networking device.

Processor 2386 can send messages and receive data, including program code, through network 2350, network link 2316 and communication interface 2315. For example, a server can store requested code for an application program (e.g., a JAVA applet) on a tangible non-volatile computer-readable storage medium to which it is connected. The server can retrieve the code from the medium and transmit it through network 2350 to communication interface 2315. The received code can be executed by processor 2386 as it is received, or stored in data storage system 2340 for later execution.

Data storage system 2340 can include or be communicatively connected with one or more processor-accessible memories configured to store information. The memories can be, e.g., within a chassis or as parts of a distributed system. The phrase "processor-accessible memory" is intended to include any data storage device to or from which processor 2386 can transfer data (using appropriate components of peripheral system 2320), whether volatile or nonvolatile; removable or fixed; electronic, magnetic, optical, chemical, mechanical, or otherwise. Exemplary processor-accessible memories include but are not limited to: registers, floppy disks, hard disks, tapes, bar codes, Compact Discs, DVDs, read-only memories (ROM), erasable programmable read-only memories (EPROM, EEPROM, or Flash), and random-access memories (RAMs). One of the processor-accessible memories in the data storage system 2340 can be a tangible non-transitory computer-readable storage medium, i.e., a non-transitory device or article of manufacture that participates in storing instructions that can be provided to processor 2386 for execution.

In an example, data storage system 2340 includes code memory 2341, e.g., a RAM, and disk 2343, e.g., a tangible computer-readable rotational storage device such as a hard drive. Computer program instructions are read into code memory 2341 from disk 2343. Processor 2386 then executes one or more sequences of the computer program instructions loaded into code memory 2341, as a result performing process steps described herein. In this way, processor 2386 carries out a computer implemented process. For example, steps of methods described herein, blocks of the flowchart illustrations or block diagrams herein, and combinations of those, can be implemented by computer program instructions. Code memory 2341 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects These aspects can all generally be referred to herein as a "service," "circuit," "circuitry," "module," or "system."

Furthermore, various aspects herein may be embodied as computer program products including computer readable program code stored on a tangible non-transitory computer readable medium. Such a medium can be manufactured as is conventional for such articles, e.g., by pressing a CD-ROM. The program code includes computer program instructions that can be loaded into processor 2386 (and possibly also other processors), to cause functions, acts, or operational steps of various aspects herein to be performed by the processor 2386 (or other processor). Computer program code for carrying out operations for various aspects described herein may be written in any combination of one or more programming language(s), and can be loaded from disk 2343 into code memory 2341 for execution. The program code may execute, e.g., entirely on processor 2386, partly on processor 2386 and partly on a remote computer connected to network 2350, or entirely on the remote computer.

The invention is inclusive of combinations of the aspects described herein. References to "a particular aspect" and the like refer to features that are present in at least one aspect of the invention. Separate references to "an aspect" (or "embodiment") or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected by a person of ordinary skill in the art within the spirit and scope of the invention.

The invention claimed is:

1. A system for measuring a sample, the system comprising:
   a) an illumination source adapted to provide electromagnetic radiation pulses at a selected temporal frequency;
   b) a microscope adapted to focus the provided electromagnetic radiation onto the sample, so that resultant electromagnetic radiation is produced by an interaction of the provided electromagnetic radiation with the sample;
   c) a plurality of optical sensors;
   d) a disperser adapted to disperse wavelengths of the resultant electromagnetic radiation onto the plurality of optical sensors; and
   e) a plurality of resonant amplifiers corresponding to respective ones of the optical detectors, each resonant amplifier operative to amplify signals having the selected temporal frequency.

2. The system according to claim 1, wherein the illumination source includes a narrowband source, a broadband source, and a combiner for providing the electromagnetic radiation pulses including electromagnetic radiation from both the narrowband source and the broadband source.

3. The system according to claim 2, further including a processor configured to temporally modulate an output power of the narrowband source or an output power of the broadband source at the selected temporal frequency.

4. The system according to claim 2, wherein the narrowband source is configured to provide ones of the electromagnetic radiation pulses having infrared wavelengths and the broadband source is configured to provide ones of the electromagnetic radiation pulses including visible and infrared wavelengths.

5. The system according to claim 2, wherein the microscope is arranged so that the sample is illuminated by the provided electromagnetic radiation from a first direction and the disperser is arranged downstream of the sample along the first direction.

6. The system according to claim 5, wherein the microscope is arranged so that the sample is illuminated by the provided electromagnetic radiation from a first direction, the disperser is arranged upstream of the sample along the first direction, and the system further includes a beam splitter arranged between the sample and the disperser.

7. The system according to claim 1, wherein the disperser is adapted to distribute a respective selected portion of the bandwidth of the received electromagnetic radiation to each of the plurality of optical sensors.

8. The system according to claim 1, further including a scanner for scanning a focal point of the provided electromagnetic radiation across the sample in an X direction and scanning the sample in a Y direction.

9. Optical detection apparatus, comprising:
   a) a plurality of optical sensors configured to provide respective electrical signals corresponding to respective incident electromagnetic radiation;
   b) a plurality of resonant amplifiers corresponding to respective optical detectors, each resonant amplifier operative to amplify portion(s) of the respective electrical signal having a selected temporal frequency and to attenuate portion(s) of the respective electrical signal not having the selected temporal frequency; and
   c) a disperser adapted to receive light and distribute a respective selected portion of an optical bandwidth of the received light to each of the plurality of optical sensors.

10. The apparatus according to claim 9, wherein each sensor includes a photodiode.

11. The apparatus according to claim 9, further including an analog-to-digital conversion unit adapted to provide digital data of respective high-frequency signals from the resonant amplifiers and of respective low-frequency signals from the optical sensors.

12. A method of analyzing constituents of a sample, the method comprising:
   contemporaneously irradiating the sample with incident radiation including narrowband light and broadband light;
   while irradiating the sample, modulating optical power of the narrowband light or the broadband light at a selected temporal frequency;
   dispersing wavelengths of resultant light from the sample across a plurality of optical detectors; and
   filtering respective signals from the optical detectors to provide a spectrum dataset of the sample, the spectrum dataset including signals corresponding to the selected temporal frequency.

13. The method according to claim 12, further including automatically performing the following steps using a processor:
   receiving a plurality of reference spectra for respective ones of the constituents; and
   mathematically fitting a combination of the reference spectra to the spectrum data of the sample, so that respective fitting coefficients for the reference spectra represent contributions of respective constituents to the sample.

14. The method according to claim 13, wherein the fitting step includes executing a multivariate curve resolution algorithm using the processor.

15. The method according to claim 12, further including changing the position of the incident radiation with respect to the sample and repeating the irradiating, modulating, dispersing, and filtering steps, so that respective spectrum datasets are provided for each of a plurality of positions of the incident radiation.

16. The method according to claim 12, wherein the filtering step includes passing the respective signals from the optical detectors through respective passive resonant bandpass filter circuits.

17. The method according to claim 12, wherein the modulating step includes modulating optical power of the narrowband light, and the dispersing step includes dispersing wavelengths of broadband resultant light across the plurality of optical detectors.

18. The method according to claim 12, further including, before the irradiating step, illuminating the plurality of optical detectors with a reference spectrum and automatically computing respective calibration data for each of the plurality of optical detectors, wherein the filtering step further includes applying the respective calibration data to the respective signals from the optical detectors.

* * * * *